US010625250B2

(12) United States Patent
Hau

(10) Patent No.: US 10,625,250 B2
(45) Date of Patent: Apr. 21, 2020

(54) PHOTOCATALYTIC SYSTEMS COMPRISING GRAPHENE AND ASSOCIATED METHODS

(71) Applicant: President and Fellows of Harvard College, Cambridge, MA (US)

(72) Inventor: Lene Vestergaard Hau, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 462 days.

(21) Appl. No.: 15/301,733

(22) PCT Filed: Apr. 3, 2015

(86) PCT No.: PCT/US2015/024359
§ 371 (c)(1),
(2) Date: Oct. 4, 2016

(87) PCT Pub. No.: WO2016/007204
PCT Pub. Date: Jan. 14, 2016

(65) Prior Publication Data
US 2017/0021344 A1 Jan. 26, 2017

Related U.S. Application Data

(60) Provisional application No. 62/003,756, filed on May 28, 2014, provisional application No. 61/975,094, filed on Apr. 4, 2014.

(51) Int. Cl.
*H01L 29/00* (2006.01)
*B01J 35/00* (2006.01)
(Continued)

(52) U.S. Cl.
CPC ........... *B01J 35/004* (2013.01); *B01J 19/127* (2013.01); *B01J 21/18* (2013.01); *B01J 31/003* (2013.01);
(Continued)

(58) Field of Classification Search
CPC .......................... B01J 35/004; H01L 29/1606
See application file for complete search history.

(56) References Cited

U.S. PATENT DOCUMENTS

| 9,755,174 | B2 * | 9/2017 | Uesaka | H01L 51/504 |
| 9,821,303 | B2 * | 11/2017 | Son | B01J 35/004 |
| 10,056,659 | B2 * | 8/2018 | Ramasamy | H01M 14/005 |
| 10,096,787 | B2 * | 10/2018 | Crowder | B82Y 30/00 |
| 2008/0308407 | A1 * | 12/2008 | Rostovtsev | C01B 3/042 |
| | | | | 204/157.47 |

(Continued)

FOREIGN PATENT DOCUMENTS

WO WO 2014/026244 A1 2/2014

OTHER PUBLICATIONS

PCT/US2015/024359, Jan. 7, 2016, International Search Report and Written Opinion.

(Continued)

*Primary Examiner* — Nicholas J Tobergte
(74) *Attorney, Agent, or Firm* — Wolf, Greenfield & Sacks, P.C.

(57) ABSTRACT

The present invention generally relates to photocatalytic systems comprising graphene and associated methods. Some embodiments are directed to systems comprising one or more layers of graphene having a first surface and a second, opposed surface. A light-absorbing complex may be associated with the first surface of the one or more graphene layers, and an electron donor complex may be associated with the light-absorbing complex. A catalytic complex may be associated with the first surface or the second surface of the one or more graphene layers. For example, the catalytic complex may catalyze the formation of hydrogen gas, NADH, and/or NADPH.

20 Claims, 18 Drawing Sheets

(51) Int. Cl.
  *C12N 9/00* (2006.01)
  *C07K 14/795* (2006.01)
  *C12N 9/96* (2006.01)
  *B01J 19/12* (2006.01)
  *B01J 21/18* (2006.01)
  *B01J 31/00* (2006.01)
  *C12N 11/14* (2006.01)
  *H01L 29/16* (2006.01)

(52) U.S. Cl.
  CPC ............ *C07K 14/795* (2013.01); *C12N 9/00* (2013.01); *C12N 9/96* (2013.01); *C12N 11/14* (2013.01); *C12Y 112/00* (2013.01); *C12Y 118/01002* (2013.01); *B01J 2219/0875* (2013.01); *B01J 2219/1203* (2013.01); *H01L 29/1606* (2013.01)

(56) References Cited

U.S. PATENT DOCUMENTS

| | | |
|---|---|---|
| 2011/0186805 A1 | 8/2011 | Bowers et al. |
| 2011/0200787 A1* | 8/2011 | Regan .................... H01J 37/20 |
| | | 428/138 |
| 2012/0097238 A1* | 4/2012 | Isaacs-Sodeye ....... B82Y 30/00 |
| | | 136/256 |
| 2016/0160364 A1* | 6/2016 | Juluri ..................... C01B 3/042 |
| | | 205/91 |

OTHER PUBLICATIONS

PCT/US2015/024359, Oct. 13, 2016, International Preliminary Report on Patentability.

* cited by examiner

PHOTOCATALYTIC SYSTEMS COMPRISING GRAPHENE AND ASSOCIATED METHODS

RELATED APPLICATIONS

This application is a national stage filing under 35 U.S.C. § 371 of International Application No. PCT/US2015/024359, filed Apr. 3, 2015, entitled "Photocatalytic Systems Comprising Graphene and Associated Methods," which claims priority under 35 U.S.C. § 119(e) to U.S. Provisional Application Ser. No. 61/975,094, filed Apr. 4, 2014, entitled "Copper Phthalocyanine-Graphene Field Effect Transistor," by Lene V. Hau, and U.S. Provisional Patent Application Ser. No. 62/003,756, filed May 28, 2014, entitled "Photocatalytic Systems Comprising Graphene and Associated Methods," by Lene V. Hau, each of which is incorporated herein by reference in its entirety.

GOVERNMENT FUNDING

This invention was made with government support under National Security Science and Engineering Faculty Fellowship No. FA9550-10-1-0208 awarded by the Office of Assistant Secretary of Defense for Research and Engineering. The government has certain rights in the invention.

FIELD

The present invention generally relates to photocatalytic systems comprising graphene and associated methods.

BACKGROUND

Systems and methods that use natural resources, such as sunlight and/or water, to catalyze the formation of fuels and other useful substances show tremendous potential. In particular, the use of naturally occurring systems, such as photosystem II (PSII), which is a protein complex involved in photosynthesis in certain plants, algae, and cyanobacteria, to produce biofuels such as diatomic hydrogen gas ($H_2$) has been appealing. However, existing attempts to use such systems have suffered a number of problems. For example, PSII can result in the formation of both diatomic oxygen gas ($O_2$) and diatomic hydrogen gas ($H_2$), raising safety concerns. Additionally, the presence of diatomic oxygen gas appears to inhibit the activity of the enzyme that catalyzes the formation of diatomic hydrogen gas. Accordingly, improved systems and methods are needed.

SUMMARY

The present invention generally relates to photocatalytic systems comprising graphene and associated methods. The subject matter of the present invention involves, in some cases, interrelated products, alternative solutions to a particular problem, and/or a plurality of different uses of one or more systems and/or articles.

Certain embodiments relate to a system comprising a layer comprising graphene, wherein the layer has a first surface and a second, opposed surface; a light-absorbing complex coupled to the first surface of the layer; and an electron donor.

In some embodiments, a system comprises a first substrate layer comprising at least one aperture; a layer comprising graphene, wherein the layer comprising graphene fully covers the at least one aperture, wherein the layer comprising graphene has a first surface and a second, opposed surface; a light-absorbing complex coupled to the first surface of the layer comprising graphene; and an electron donor.

Certain embodiments relate to methods. In some embodiments, the method comprises providing a system comprising: a layer comprising graphene, wherein the layer has a first surface and a second, opposed surface; a light-absorbing complex coupled to the first surface of the layer; and an electron donor. In some embodiments, the method further comprises exposing the system to light. In certain embodiments, the method further comprises exposing the system to water.

In some embodiments, a method comprises providing a system comprising: a first substrate layer comprising at least one aperture; a layer comprising graphene, wherein the layer comprising graphene fully covers the at least one aperture, wherein the layer comprising graphene has a first surface and a second, opposed surface; a light-absorbing complex coupled to the first surface of the layer comprising graphene; and an electron donor. In some embodiments, the method further comprises exposing the system to light. In certain embodiments, the method further comprises exposing the system to water.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
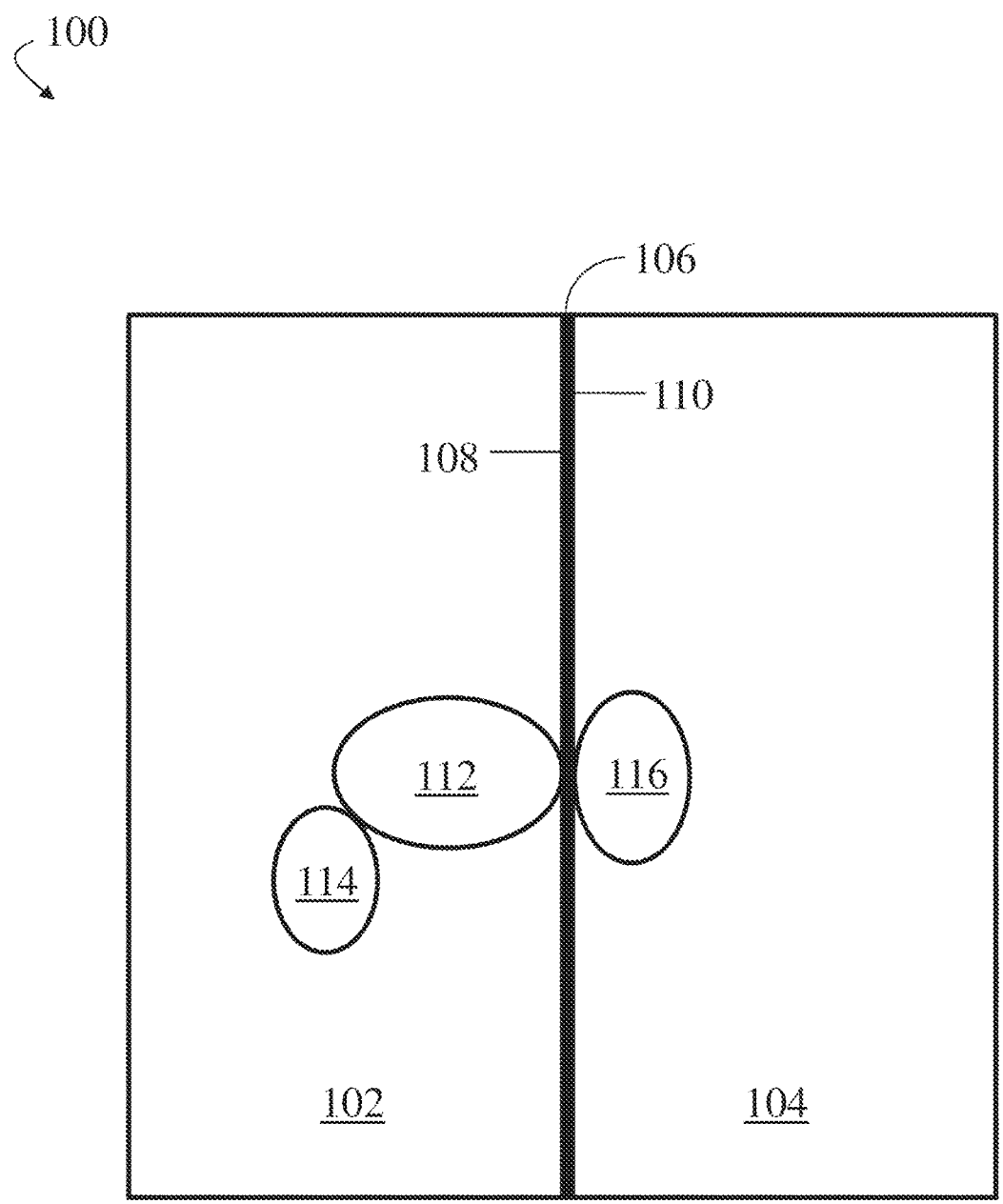
FIG. 1A is an exemplary schematic illustration of a system comprising a graphene layer, according to some embodiments.

Embodiments described herein generally relate to photocatalytic systems comprising graphene and associated methods. The ability to use a natural resource, such as sunlight, to catalyze the formation of fuels and other useful substances is tremendously appealing. For example, a system that uses sunlight to catalyze the formation of diatomic hydrogen gas (i.e., $H_2$) can advantageously provide a clean, renewable energy source. Some embodiments described herein are directed to systems that comprise a layer of graphene separating a first reservoir and a second reservoir. A first surface of the graphene layer, which is exposed to the first reservoir, may be coupled to a light-absorbing complex. The light-absorbing complex may, in some cases, be associated with an electron donor. A second, opposed surface of the graphene layer, which is exposed to the second reservoir, may be coupled to a catalytic complex that catalyzes the formation of certain compounds. For example, the catalytic complex may catalyze the formation of diatomic hydrogen gas, nicotinamide adenine dinucleotide (NADH), and/or nicotinamide adenine dinucleotide phosphate (NADPH). As discussed further herein, the unique properties of graphene may allow electrons to be transferred from the light-absorbing complex coupled to the first surface of the graphene layer to the catalytic complex coupled to the second surface of the graphene layer. In the systems described herein, the first reservoir may be separated from the second reservoir, such that certain molecules cannot travel from the first reservoir to the second reservoir, or from the second reservoir to the first reservoir. For example, the system that catalyzes the formation of diatomic hydrogen gas may be configured such that diatomic oxygen gas (i.e., $O_2$) formed in the first reservoir cannot pass to the second reservoir, and diatomic hydrogen gas formed in the second reservoir cannot pass to the first reservoir. Such a configuration may advantageously allow diatomic oxygen gas to be kept separate from diatomic hydrogen gas, reducing safety concerns and preventing inhibition of catalytic activity relating to the formation of diatomic hydrogen gas. Further, in some cases, separating the diatomic oxygen gas from the diatomic hydrogen gas may advantageously allow chemical potential energy (e.g., energy stored in the $H_2$ bonds and the $O_2$ bonds) to be stored and/or harnessed. For example, in certain embodiments, the diatomic hydrogen gas and/or diatomic oxygen gas may be fed to a fuel cell, which may convert the chemical potential energy of the diatomic hydrogen gas and/or diatomic oxygen gas to electrical energy. In contrast, if the diatomic hydrogen gas and diatomic oxygen gas were to combine within the system (e.g., in the first reservoir and/or second reservoir), the highly exothermic reaction would result in the formation of water and the generation of heat, and the chemical potential energy of the diatomic hydrogen gas and diatomic oxygen gas would be wasted. Some embodiments described herein are directed to methods of forming a chemical compound upon exposure to light (e.g., sunlight).

An exemplary schematic illustration of a photocatalytic system comprising graphene is shown in FIG. 1A. In FIG. 1A, system 100 comprises a first reservoir 102 and a second reservoir 104. First reservoir 102 may be separated from second reservoir 104 by a layer 106 comprising one or more layers of graphene. In some cases, graphene layer 106 comprises a plurality of holes. In certain embodiments, each hole of the plurality of holes has a largest dimension (e.g., diameter) that is sufficiently small that a hydrogen ion ($H^+$) can pass through the hole, but a diatomic oxygen gas molecule and/or a diatomic hydrogen gas molecule cannot pass through the hole. As shown in FIG. 1A, graphene layer 106 has a first surface 108 that is exposed to first reservoir 102 and a second, opposed surface 110 that is exposed to second reservoir 104. A light-absorbing complex 112 is coupled to first surface 108. As discussed in further detail herein, a light-absorbing complex generally refers to one or more molecules where absorption of a photon within a certain wavelength range can lead to excitation of an electron (e.g., from a ground electronic state to an excited electronic state). In some embodiments, an electron donor 114 is associated with light-absorbing complex 112. Generally, an electron donor refers to one or more molecules capable of donating at least one electron to another molecule. Electron donor 114 may, in certain cases, comprise an oxygen-evolving complex (e.g., a water-splitting complex that is capable of splitting water molecules into diatomic oxygen gas, hydrogen ions, and electrons). In certain embodiments, reservoir 102 contains an amount of water. As shown in FIG. 1A, a catalytic complex 116 is coupled to second surface 110 of graphene layer 106. Catalytic complex 116 may be capable of catalyzing the formation of one or more chemical compounds, such as diatomic hydrogen gas, NADH, and/or NADPH.

In operation, a source of light (not shown) may emit a photon having a wavelength within the absorption spectrum of light-absorbing complex 112. In certain cases, the source of light is the sun. Light-absorbing complex 112 may absorb the photon, and an electron may be excited. The excited electron may then be transferred to (e.g., injected into) graphene layer 106. In certain cases, the excited electron may be transferred from light-absorbing complex 112 to graphene layer 106 through one or more intermediate molecules. The excited electron may subsequently be transferred from graphene layer 106 to catalytic complex 116. In some cases, the excited electron is transferred from graphene layer 106 to catalytic complex 116 through one or more intermediate molecules. In some cases, electron donor 114 donates an electron to light-absorbing complex 112, replacing the excited electron. In certain embodiments, the electron donation from electron donor 114 to light-absorbing complex 112 occurs through one or more intermediate molecules. In certain embodiments, electron donor 114 is an oxygen-evolving complex, and the donated electron is produced through a chemical reaction in which two water molecules are split to form diatomic oxygen gas, four hydrogen ions, and four electrons. In some cases, at least two of the hydrogen ions formed from the water-splitting chemical reaction pass through one or more holes in graphene layer 106, traveling from first reservoir 102 to second reservoir 104. In second reservoir 104, catalytic complex 116 may catalyze a chemical reaction. For example, two hydrogen ions and two electrons may be combined to form diatomic hydrogen gas.

Figure 1B:
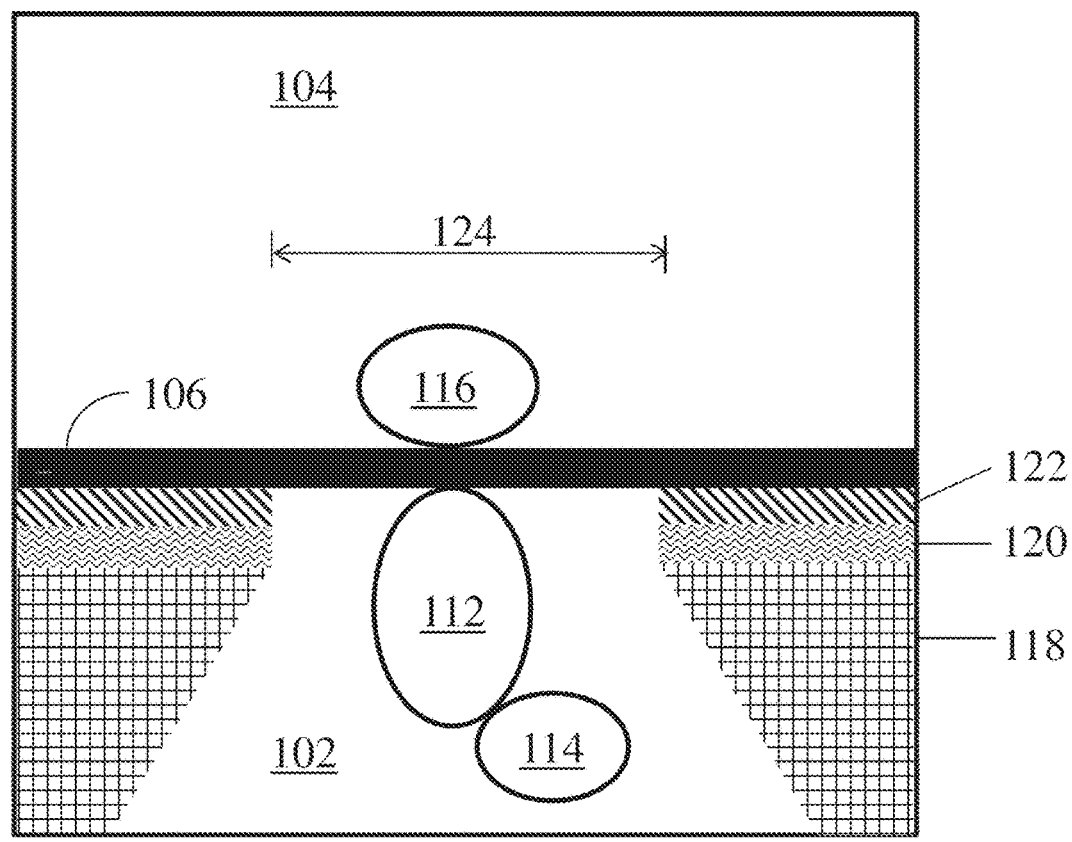
FIG. 1B is an exemplary schematic illustration of a system comprising a graphene layer and one or more substrate layers, according to some embodiments.

In some systems described herein, one or more graphene layers are fully extended across (e.g., fully cover) one or more apertures in one or more substrate layers. As discussed in further detail herein, the one or more substrate layers may advantageously provide support to the one or more graphene layers. An exemplary schematic illustration of a system comprising graphene and one or more substrate layers is shown in FIG. 1B. In FIG. 1B, system 100 comprises first reservoir 102 and second reservoir 104, where first reservoir 102 is separated from second reservoir 104 by a layer 106 comprising one or more layers of graphene. Reservoirs 102 and 104 are arranged such that first reservoir 102 is positioned directly below second reservoir 104. In some embodiments, graphene layer 106 is at least partially supported by first substrate layer 118. First substrate layer 118 may comprise an electrically conductive material (e.g., a metal, a semiconductor) or an electrically insulating material. Non-limiting examples of suitable electrically conductive materials include silicon, germanium, gallium nitride, gallium phosphide, gallium arsenide, indium gallium arsenide, copper, aluminum, silver, gold, platinum, nickel, and any combinations thereof. Examples of suitable electrically insulating materials include, but are not limited to, silicon dioxide ($SiO_2$) (e.g., quartz, fused silica), silicon nitride ($Si_3N_4$), hexagonal boron nitride (BN), aluminum oxide ($Al_2O_3$) (e.g., sapphire), and any combinations thereof. First substrate layer 118 may, in certain cases, comprise silicon (e.g., a silicon wafer). In some embodiments, graphene layer 106 is at least partially supported by optional second substrate layer 120. Second substrate layer 120 may, in certain embodiments, comprise one or more layers comprising silicon dioxide ($SiO_2$), silicon nitride ($Si_3N_4$), hexagonal boron nitride (BN), aluminum oxide ($Al_2O_3$), and/or octadecyltrichlorosilane ("OTS"). In some embodiments, graphene layer 106 is at least partially supported by optional third substrate layer 122. Third substrate layer 122 may, in some cases, enhance adhesion between graphene layer 106 and first substrate layer 118 and/or second substrate layer 120. In certain cases, third substrate layer 122 comprises silicon dioxide, hexagonal boron nitride, and/or OTS. In a particular, non-limiting embodiment, second substrate layer 120 comprises silicon dioxide and third substrate layer 122 comprises OTS. In such an embodiment, the second substrate layer and/or the third substrate layer may advantageously comprise alkyl-terminated silicon dioxide. In certain cases, alkyl-terminated silicon dioxide may improve certain electrical properties of the graphene layer (e.g., avoid charge traps). As shown in FIG. 1B, there may be an aperture in the one or more substrate layers, and graphene layer 106 may be fully extended (e.g., suspended) across the aperture. The aperture may have a largest dimension (e.g., diameter) 124, as indicated in FIG. 1B.

Figure 1C:
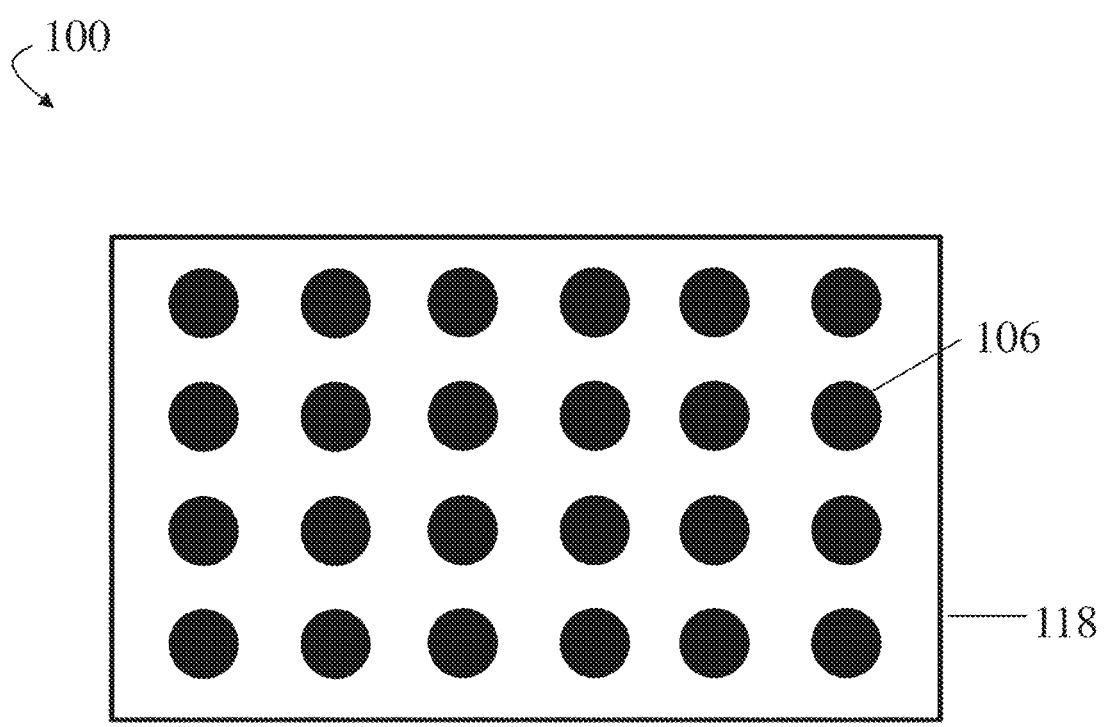
FIG. 1C is an exemplary schematic illustration, according to some embodiments, of a plurality of apertures in one or more substrate layers.
Figure 2A:
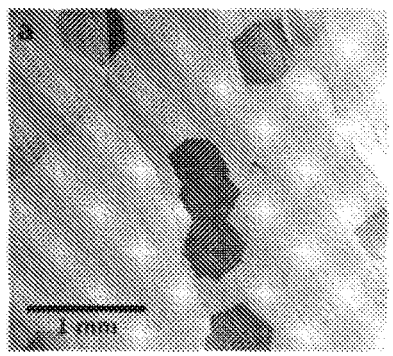
FIG. 2A shows an SEM images of an exemplary suspended graphene device, according to some embodiments, after a synthesis time of 30 minutes.
Figure 2B:
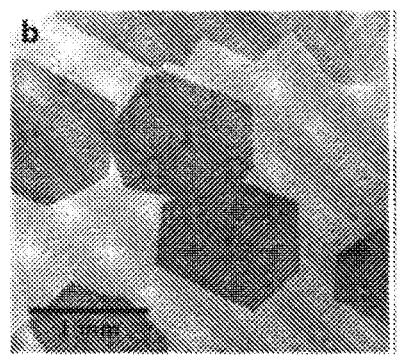
FIG. 2B shows an SEM image of an exemplary suspended graphene device, according to some embodiments, after a synthesis time of 60 minutes.
Figure 2C:
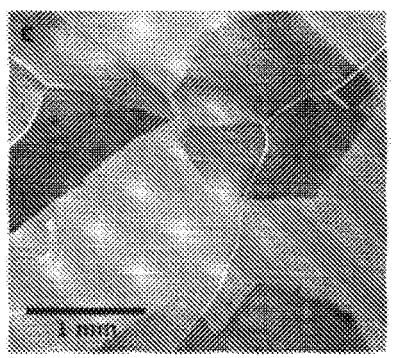
FIG. 2C shows an SEM image of an exemplary suspended graphene device, according to some embodiments, after a synthesis time of 120 minutes.
Figure 2D:
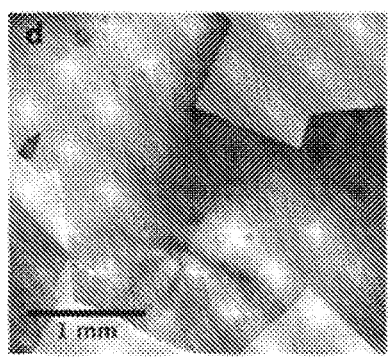
FIG. 2D shows an SEM image of an exemplary suspended graphene device, according to some embodiments, after a synthesis time of 180 minutes.

In some embodiments, one or more substrate layers comprise a plurality of apertures. FIG. 1C depicts an exemplary schematic illustration of a top view of system 100. In FIG. 1C, system 100 comprises a substrate layer 118, which has a plurality of apertures through which a graphene layer 106 can be seen. In FIG. 1C, system 100 comprises 24 apertures. However, a system as described herein may comprise any number of apertures. In some embodiments, a system comprises at least 5 apertures, at least 10 apertures, at least 20 apertures, at least 50 apertures, at least 100 apertures, at least 200 apertures, at least 500 apertures, or at least 1000 apertures. In some embodiments, a system comprises less than 1000 apertures, less than 500 apertures, less than 200 apertures, less than 100 apertures, less than 50 apertures, less than 20 apertures, less than 10 apertures, or less than 5 apertures. In some embodiments, a system comprises a number of apertures in the range of 5 to 100, 5 to 200, 5 to 500, 5 to 1000, 100 to 200, 100 to 500, 100 to 1000, 200 to 500, 200 to 1000, or 500 to 1000 apertures.

Some embodiments are directed to a system comprising a light-absorbing complex coupled to a surface of one or more graphene layers. In some embodiments, the light-absorbing complex is coupled to the first surface of one or more graphene layers. A light-absorbing complex generally refers to one or more molecules where absorption of a photon within a certain wavelength range (i.e., absorption spectrum) can lead to excitation of an electron (e.g., from a ground electronic state to an excited electronic state). In some embodiments, the light-absorbing complex comprises a molecule belonging to at least one of the following classes of compounds: chlorophylls, porphyrins, hemes, and/or phthalocyanines. Non-limiting examples of suitable molecules include P680 (e.g., a chlorophyll dimer that is present in photosystem II), P700 (e.g., a chlorophyll dimer that is present in photosystem I), zinc phthalocyanine, copper phthalocyanine, zinc porphyrin, zinc tetraphenylporphyrin (TPP), and beta-carotene. In some embodiments, the light-absorbing complex comprises one or more proteins and/or one or more coenzymes (e.g., cofactors). For example, the light-absorbing complex may further comprise one or more plastoquinone A (PQ-A) molecules and/or one or more plastoquinone B (PQ-B) molecules. In some embodiments, PQ-A and/or PQ-B may be capable of accepting one or more electrons from another portion of the light-absorbing complex (e.g., P680).

The light-absorbing complex may be capable of absorbing light from any portion of the electromagnetic spectrum. In some embodiments, the light-absorbing molecule absorbs visible light. As used herein, "visible light" is given its ordinary meaning in the art and generally refers to light having a wavelength in the range of about 390 nm to about 740 nm. In some embodiments, the light-absorbing complex is capable of absorbing light having a wavelength in the blue and/or violet portion of the electromagnetic spectrum (e.g., from about 390 nm to about 495 nm). In some embodiments, the light-absorbing complex is capable of absorbing light having a wavelength in the red portion of the electromagnetic spectrum (e.g., from about 620 nm to about 740 nm). The light-absorbing complex may, in some cases, be capable of absorbing radiation having a wavelength in the ultraviolet portion of the electromagnetic radiation spectrum (e.g., from about 100 nm to about 390 nm) and/or in the infrared portion of the electromagnetic radiation spectrum (e.g., above about 740 nm). In some embodiments, the light-absorbing complex is capable of absorbing radiation having a wavelength of at least about 100 nm, at least about 200 nm, at least about 300 nm, at least about 390 nm, at least about 400 nm, at least about 450 nm, at least about 500 nm, at least about 550 nm, at least about 600 nm, at least about 650 nm, at least about 700 nm, at least about 740 nm, at least about 800 nm, at least about 900 nm, or at least about 1 micron. In some embodiments, the light-absorbing complex is capable of absorbing radiation having a wavelength of about 1 micron or less, about 900 nm or less, about 800 nm or less, about 750 nm or less, about 740 nm or less, about 700 nm or less, about 650 nm or less, about 600 nm or less, about 550 nm or less, about 500 nm or less, about 450 nm or less, about 400 nm or less, about 390 nm or less, about 300 nm or less, about 200 nm or less, or about 100 nm or less. In certain embodiments, the light-absorbing complex is capable of absorbing radiation having a wavelength in the range of about 100 nm to about 300 nm, about 100 nm to about 400 nm, about 100 nm to about 700 nm, about 100 nm to about 740 nm, about 100 nm to about 1 micron, about 300 nm to about 400 nm, about 300 nm to about 700 nm, about 300 nm to about 740 nm, about 300 nm to about 1 micron, about 390 nm to about 680 nm, about 390 nm to about 700 nm, about 390 nm to about 740 nm, about 400 nm to about 680 nm, about 400 nm to about 700 nm, about 400 nm to about 740 nm, about 400 nm to about 1 micron, 700 nm to about 1 micron, or about 740 nm to about 1 micron.

The light-absorbing complex may be coupled to the one or more layers of graphene according to any method known in the art. In some embodiments, at least a portion of the light-absorbing complex is adsorbed to a graphene layer. In some cases, at least a portion of the light-absorbing complex is covalently bound to at least a portion of a graphene layer. In some cases, at least a portion of the light-absorbing complex is non-covalently bound to at least a portion of a graphene layer. For example, at least a portion of the light-absorbing complex may be non-covalently bound to at least a portion of the graphene layer through pi stacking interactions between one or more aromatic rings of the light-absorbing complex and one or more aromatic rings of the graphene layer. In some embodiments, at least a portion of the light-absorbing complex is non-covalently bound to a graphene layer through electrostatic forces and/or van der Waals forces. In certain embodiments, the light-absorbing complex is coupled to a graphene layer through one or more binding molecules. The light-absorbing complex may, in some cases, be associated with the one or more binding molecules through covalent and/or non-covalent binding. The one or more binding molecules may, in some cases, be associated with a graphene layer through covalent and/or non-covalent binding. For example, the light-absorbing complex may be covalently linked to one or more pyrene molecules (e.g., through one or more cysteines). According to certain embodiments, one or more cysteines of a portion of the light-absorbing complex may be covalently linked to a binding molecule. In some cases, a first end of the binding molecule comprises a moiety capable of reacting with a cysteine (e.g., a maleimide). In certain cases, a second end of the binding molecule comprises one or more pyrenes. The one or more pyrene molecules may be non-covalently associated with a graphene layer through pi stacking. In some embodiments, the binding molecule may comprise one or more atoms (e.g., carbon atoms) between the first end (e.g., a maleimide group) and the second end (e.g., a pyrene group) of the binding molecule. The one or more atoms may, in certain embodiments, form a linear carbon chain. The length of the binding molecule may, for example, affect the distance between the light-absorbing complex and the graphene layer. In some embodiments, the binding molecule comprises at least 1, at least 2, at least 5, at least 10, at least 20, at least 50, or at least 100 atoms (e.g., carbon atoms) between the first end and the second end of the binding molecule. In some embodiments, the binding molecule comprises about 100 atoms or less, about 50 atoms or less, about 20 atoms or less, about 10 atoms or less, about 5 atoms or less, about 2 atoms or less, about 1 atom or less, or about 0 atoms between the first end and the second end of the binding molecule. In some embodiments, the number of atoms between the first end and the second end of the binding molecule is in the range of 0 to 2, 0 to 5, 0 to 10, 0 to 20, 0 to 50, 0 to 100, 2 to 5, 2 to 10, 2 to 20, 2 to 50, 2 to 100, 10 to 20, 10 to 50, 10 to 100, 20 to 50, 20 to 100, or 50 to 100.

The light-absorbing complex may be coupled to either the first surface of a graphene layer or the second, opposed surface of a graphene layer. In some embodiments, more than one light-absorbing complex is coupled to a graphene layer. In certain cases, more than one light-absorbing complex is coupled to the same (e.g., first or second) surface of a graphene layer. In some embodiments, at least one light-absorbing complex is coupled to the first surface of a graphene layer and at least one light-absorbing complex is coupled to the second surface of a graphene layer. The at least one light-absorbing complex coupled to the first surface of a graphene layer and the at least one light-absorbing complex coupled to the second surface of a graphene layer may be the same type of light-absorbing complex (e.g., a light-absorbing complex of PSII) or may be different types of light-absorbing complexes (e.g., a light-absorbing complex of PSII and a light-absorbing complex of PSI). For example, in a particular, non-limiting embodiment, the light-absorbing complex of PSII may be coupled to a first surface of a graphene layer (e.g., via a PQ-A molecule), and the light-absorbing complex of PSI may be coupled to a second surface of a graphene layer (e.g., via P700). In certain embodiments, a catalytic complex (e.g., a hydrogenase) may be coupled to the PSI light-absorbing complex (e.g., via an iron-sulfur complex) or may be in solution in the second reservoir in contact with the second surface of the graphene layer.

Some embodiments are directed to a system comprising an electron donor. In some embodiments, a system comprises a plurality of electron donors. As used herein, an electron donor refers to one or more molecules capable of donating at least one electron to another molecule (e.g., the light-absorbing complex). In certain embodiments, the electron donor comprises an oxygen-evolving complex (e.g., a water-splitting complex), which performs the following oxidation of water:

$$2H_2O \rightarrow O_2 + 4H^+ + 4e^-$$

That is, the oxygen-evolving complex is capable of splitting two water molecules to form diatomic oxygen gas, four hydrogen ions, and four electrons. The oxygen-evolving complex may, in certain embodiments, comprise at least one manganese ion and/or at least one calcium ion. In some embodiments, the electron donor comprises one or more sacrificial electron donors (e.g., an electron donor that is consumed in the process of donating an electron). Non-limiting examples of suitable sacrificial electron donors include ascorbic acid and ethylenediaminetetraacetic acid (EDTA). In some embodiments, the electron donor comprises ferrocene and/or ferrodoxin. In some embodiments, the electron donor is in solution in a solvent (e.g., water).

The electron donor may be associated with the light-absorbing complex according to any method known in the art. In some embodiments, at least a portion of the electron donor is covalently or non-covalently bound to at least a portion of the light-absorbing complex. In some embodiments, the electron donor is associated with the light-absorbing complex through one or more binding molecules. The one or more binding molecules may, in some cases, be covalently or non-covalently linked to the electron donor. In some cases, the one or more binding molecules may be covalently or non-covalently linked to the light-absorbing complex. In some embodiments, the electron donor is neither covalently nor non-covalently associated with the light-absorbing complex. The electron donor's sole association with the light-absorbing complex may be through the donation of an electron from the electron donor to the light-absorbing complex.

In some embodiments, the system further comprises an electron acceptor. In certain cases, the system comprises a plurality of electron acceptors. Generally, an electron acceptor refers to one or more molecules capable of accepting at least one electron from another molecule (e.g., the light-absorbing complex, the electron donor). In some embodiments, at least one electron may be transferred from the light-absorbing complex to at least one electron acceptor. In some cases, at least one electron may be transferred from at least one electron acceptor to a graphene layer. In some embodiments, at least one electron may be transferred to at least two electron acceptors. In some embodiments, one or more molecules may be capable of acting as both an electron donor and an electron acceptor. A non-limiting example of a suitable electron acceptor is cytochrome c. As discussed in further detail below, in some cases, the electron acceptor is photosystem I (PSI).

In some embodiments, the light-absorbing complex comprises the light-absorbing complex of photosystem II. In some embodiments, the electron donor comprises the oxygen-evolving complex of photosystem II (PSII). Generally, PSII refers to a protein complex that naturally occurs in the thylakoid membrane of certain plants, algae, and cyanobacteria. Although the structure and composition of PSII depend on the species in which it is found, PSII generally comprises a light-absorbing complex comprising a chlorophyll molecule referred to as P680. P680 is generally capable of absorbing a photon having a wavelength within its absorption spectrum (which generally has a maximum at 680 nm), resulting in an excited electron. In PSII, the excited electron may be transferred through a plurality of coenzymes and cofactors to reduce a plastoquinone (e.g., PQ-A, PQ-B) to plastoquinol. In some cases, the light-absorbing complex of PSII comprises one or more plastoquinone A (PQ-A) molecules and/or one or more plastoquinone B (PQ-B) molecules. PSII also generally comprises an oxygen-evolving complex that oxidizes water to form diatomic oxygen gas, hydrogen ions, and electrons. In certain cases, the oxygen-evolving complex comprises four manganese ions and one calcium ion. In some cases, at least one of the electrons formed through water splitting is used to replace at least one excited electron lost by the light-absorbing complex. The donation of an electron to the light-absorbing complex may, in some cases, prevent unproductive back electron transfer. In addition to a light-absorbing complex and/or an oxygen-evolving complex, PSII may further comprise a plurality of subunits and coenzymes (e.g., cofactors).

In some embodiments, the system comprises a PSII complex that has been isolated from a biological source. For example, the PSII complex may have been isolated from a plant, alga, or cyanobacterium. In certain embodiments, the PSII complex has been isolated from a BP-1 strain of thermophilic cyanobacteria and/or from *Synechocystis* sp. PCC6803. In some embodiments, the PSII complex has been isolated from spinach. In some embodiments, the system comprises a synthetic PSII complex (e.g., a man-made PSII complex, such as one that is expressed from recombinant nucleic acid molecules). For example, one or more genes encoding expression of a PSII complex may be altered through site-directed mutagenesis. In certain embodiments, one or more lysines in the PSII complex may be mutated to be cysteines.

In some embodiments, a PSII complex associated with a layer of graphene is oriented such that a portion of the light-absorbing complex is in close proximity to the graphene layer and the oxygen-evolving complex is located further from the graphene layer. Such an orientation may be advantageous, in certain cases, because it may allow the light-absorbing complex to easily inject an excited electron into the graphene layer (e.g., before the excited electron relaxes to its ground state). In certain embodiments, a plastoquinone A (PQ-A) molecule of the PSII complex is in close proximity to the graphene layer and P680 of the PSII complex is located further from the graphene layer. In some embodiments, the distance between PQ-A and the graphene layer is about 100 angstroms or less, about 50 angstroms or less, about 20 angstroms or less, about 10 angstroms or less, about 5 angstroms or less, or about 1 angstrom. In certain cases, the distance between PQ-A and the graphene layer is in the range of about 1 angstrom to about 5 angstroms, about 1 angstrom to about 10 angstroms, about 1 angstrom to about 20 angstroms, about 1 angstrom to about 50 angstroms, or about 1 angstrom to about 100 angstroms.

In some cases, the PSII complex may be oriented through application of an electric field (e.g., application of a voltage between the graphene layer and an electrode in solution in the first or second reservoir). The PSII complex generally has an electric dipole moment. A voltage may be selected such that PSII is appropriately oriented on the graphene layer. In some embodiments, the voltage is at least about 10 mV, at least about 20 mV, at least about 50 mV, or at least about 100 mV. In some embodiments, the voltage is about 100 mV or less, about 50 mV or less, about 20 mV or less, or about 10 mV or less. In certain embodiments, the voltage is in the range of about 10 mV to about 20 mV, about 10 mV to about 50 mV, about 10 mV to about 100 mV, about 20 mV to about 50 mV, about 20 mV to about 100 mV, or about 50 mV to about 100 mV. In some embodiments, the graphene is at a negative potential relative to the electrode. In some embodiments, the graphene is at a positive potential relative to the electrode. In some embodiments, the graphene is initially at a negative potential and subsequently is at a positive potential. For example, the graphene may initially be at a negative potential to appropriately align the PSII complex with respect to the graphene, and may subsequently be at a positive potential to draw it onto the graphene surface. In some cases, a positive potential has a lower magnitude than a negative potential. For example, the positive potential may have a magnitude that is at least about 2 times smaller, at least about 5 times smaller, or at least about 10 times smaller than the magnitude of the negative potential. In some embodiments, the graphene layer may comprise one or more holes, and the PSII complex may be drawn into the one or more holes. In some embodiments, the one or more holes have a diameter of at least about 10 nm, at least about 20 nm, at least about 50 nm, or at least about 100 nm. In some embodiments, the one or more holes have a diameter of about 100 nm or less, about 50 nm or less, about 20 nm or less, or about 10 nm or less. In some embodiments, the one or more holes may advantageously be good binding sites due to free carbon bonds and carboxyl groups at the hole edges.

It should be recognized that any number of molecules may be associated with a surface (e.g., a first surface or a second surface) of a graphene layer. For example, at least two, at least five, at least ten, at least twenty, or at least fifty molecules may be associated with a surface of a graphene layer. In some embodiments, a plurality of the molecules comprise a light-absorbing complex. In some embodiments, each of the molecules comprises a light-absorbing complex. In some embodiments, a plurality of the molecules comprise PSII. In some embodiments, each of the molecules comprises PSII. In some embodiments, at least one of the molecules does not comprise a light-absorbing complex. In certain cases, at least one of the molecules does not comprise PSII.

In some embodiments, a photosystem I (PSI) complex is coupled to a surface of a graphene layer. In some embodiments, a photosystem I (PSI) complex is coupled to a first surface of a graphene layer. PSI generally refers to a protein complex that naturally occurs in certain plants, algae, and bacteria, and that harnesses light to reduce $NADP^+$ to NADPH. Although the structure and composition of PSI depend on the species in which it is found, PSI generally comprises a light-absorbing complex comprising a chlorophyll molecule referred to as P700. P700 is generally capable of absorbing a photon having a wavelength within its absorption spectrum (which generally has a maximum of about 700 nm), resulting in an excited electron. In some embodiments, the excited electron is transferred to a coenzyme and/or cofactor of PSI. In some embodiments, the excited electron is transferred to the graphene layer. In certain cases, the excited electron is transferred to the graphene layer through one or more intermediate molecules. The excited electron may subsequently be transferred to another molecule coupled to a surface of the graphene layer, such as a catalytic complex. The electron transfer may, in some cases, occur through one or more intermediate molecules. PSI may also comprise an iron-sulfur complex. Additionally, PSI may further comprise a plurality of subunits and/or a plurality of coenzymes and cofactors.

According to some embodiments, PSI acts as an electron acceptor. For example, the absorption of a photon within the absorption spectrum of P700 and the subsequent excitation of an electron from the ground state to an excited state may result in a vacancy in the ground state of P700. In some cases, an electron (e.g., an electron from PSII, an electron from the graphene layer) may be transferred to a P700 molecule of PSI (e.g., to the ground state of the P700 molecule of PSI).

In some embodiments, a PSI complex associated with a layer of graphene is oriented such that a portion of the PSI complex is in close proximity to the graphene layer. For example, in certain cases, P700 is positioned in close proximity to the surface of the graphene layer. In some cases, the distance between P700 and the graphene layer is about 100 angstroms or less, about 50 angstroms or less, about 20 angstroms or less, about 10 angstroms or less, about 5 angstroms or less, or about 1 angstrom. In certain cases, the distance between P700 and the graphene layer is in the range of about 1 angstrom to about 5 angstroms, about 1 angstrom to about 10 angstroms, about 1 angstrom to about 20 angstroms, about 1 angstrom to about 50 angstroms, or about 1 angstrom to about 100 angstroms.

PSI may be oriented on the surface of a graphene layer using any method described above for orienting PSII. For example, in some cases, the PSI complex may be oriented through application of an electric field. The PSI complex generally has an electric dipole moment. A voltage may be selected such that PSI is appropriately oriented on the graphene layer (e.g., such that the light-absorbing complex is in close proximity to the graphene layer). In some embodiments, the voltage is at least about 10 mV, at least about 20 mV, at least about 50 mV, or at least about 100 mV. In some embodiments, the voltage is about 100 mV or less, about 50 mV or less, about 20 mV or less, or about 10 mV or less. In certain embodiments, the voltage is in the range of about 10 mV to about 20 mV, about 10 mV to about 50 mV, about 10 mV to about 100 mV, about 20 mV to about 50 mV, about 20 mV to about 100 mV, or about 50 mV to about 100 mV. In some embodiments, the graphene is at a negative potential relative to the electrode. In some embodiments, the graphene is at a positive potential relative to the electrode. In some embodiments, the graphene is initially at a negative potential and subsequently is at a positive potential. For example, the graphene may initially be at a negative potential to appropriately align the PSI complex with respect to the graphene, and may subsequently be at a positive potential to draw it onto the graphene surface. In some cases, a positive potential has a lower magnitude than a negative potential. For example, the positive potential may have a magnitude that is at least about 2 times smaller, at least about 5 times smaller, or at least about 10 times smaller than the magnitude of the negative potential. As noted above, the graphene layer may comprise one or more holes, and the PSI complex may be drawn into the one or more holes.

In some embodiments, at least one molecule is coupled to a surface of a layer of graphene. In some embodiments, the at least one molecule is coupled to a surface of a layer of graphene that is opposite to the surface that a light-absorbing complex is coupled to (e.g., if a light-absorbing complex is coupled to the first surface, the at least one molecule is coupled to the second surface). The at least one molecule may, in certain embodiments, be coupled to the second surface of a layer of graphene. In some embodiments, the at least one molecule is coupled to the same surface of a layer of graphene that a light-absorbing complex is coupled to (e.g., the light-absorbing complex and the at least one molecule are both coupled to a first surface of a layer of graphene).

In some cases, the at least one molecule may be a catalytic complex (e.g., one or more molecules capable of catalyzing at least one chemical reaction). In some embodiments, the catalytic complex is capable of catalyzing the reduction of protons to form diatomic hydrogen ($H_2$), as shown in the following reaction:

$$2H^+ + 2e^- \rightarrow H_2$$

In some embodiments, the catalytic complex comprises a hydrogenase (e.g., an enzyme catalyzing the reduction of protons). In certain cases, the hydrogenase has an active site comprising at least one metal atom. The at least one metal atom may, in some cases, comprise one iron atom (e.g., [Fe]-only), two iron atoms (e.g., [FeFe]), and/or nickel and iron (e.g., [NiFe]). In some embodiments, the at least one molecule comprises platinum. In some embodiments, the at least one molecule comprises at least one nanoparticle. The at least one nanoparticle may, in certain cases, comprise platinum, iron, nickel, or any combination thereof. In certain embodiments, the hydrogenase, platinum, and/or at least one nanoparticle are coupled to a surface of a layer of graphene that is opposite to the surface to which a light-absorbing complex is coupled.

In some embodiments, the catalytic complex is capable of catalyzing the reduction of $NADP^+$ to form NADPH. In some embodiments, the catalytic complex comprises ferredoxin-$NADP^+$ reductase ("FNR") (e.g., an enzyme that catalyzes the oxidation of ferredoxin and the reduction of $NADP^+$). Ferredoxin-$NADP^+$ reductase can catalyze the formation of NADPH. In some cases, NADPH may advantageously be used as a reducing power to assimilate carbon dioxide. For example, NADPH may be used to turn carbon dioxide into glucose. In some cases, NADPH may be used to form one or more alcohols (e.g., methanol, ethanol). For example, NADPH may be used by an enzyme that catalyzes the formation of an alcohol (e.g., the conversion of methane to methanol). In some embodiments, the catalytic complex further comprises one or more cofactors. For example, the catalytic complex may comprise a flavin cofactor (e.g., flavin adenine dinucleotide). Without wishing to be bound by a particular theory, the flavin cofactor may accept two electrons and combine the two electrons with one proton and $NADP^+$ to form NADPH.

In certain embodiments, FNR is coupled to a surface of a layer of graphene that is opposite to the surface to which a light-absorbing complex is coupled. In some embodiments, FNR is coupled to the same surface of a layer of graphene to which a light-absorbing complex is coupled.

In some embodiments, the catalytic complex is capable of catalyzing the reduction of $NAD^+$ to form NADH. In certain cases, the catalytic complex comprises ferredoxin-$NAD^+$ reductase (e.g., an enzyme that catalyzes the oxidation of ferredoxin and the reduction of $NAD^+$).

The catalytic complex may be coupled to a surface of a graphene layer according to any method known in the art. For example, at least a portion of the catalytic complex may be covalently or non-covalently bound to at least a portion of the graphene layer. In some embodiments, the catalytic complex may be covalently or non-covalently bound to one or more binding molecules, which may be covalently or non-covalently bound to the graphene layer. According to some embodiments, a catalytic complex associated with a layer of graphene is oriented such that a portion of the catalytic complex is in close proximity to the graphene layer. In some embodiments, the distance between an electron-mediating part of the catalytic complex and the graphene layer is about 100 angstroms or less, about 50 angstroms or less, about 20 angstroms or less, about 10 angstroms or less, about 5 angstroms or less, or about 1 angstrom. In certain cases, the distance between an electron-mediating part of the catalytic complex and the graphene layer is in the range of about 1 angstrom to about 5 angstroms, about 1 angstrom to about 10 angstroms, about 1 angstrom to about 20 angstroms, about 1 angstrom to about 50 angstroms, or about 1 angstrom to about 100 angstroms. In certain embodiments (e.g., embodiments in which the catalytic complex comprises FNR), the catalytic complex is oriented such that a flavin cofactor (e.g., flavin adenine dinucleotide) is positioned in close proximity to a surface of the graphene layer. In some cases, the distance between a flavin cofactor of the catalytic complex and the graphene layer is about 100 angstroms or less, about 50 angstroms or less, about 20 angstroms or less, about 10 angstroms or less, about 5 angstroms or less, about 2 angstroms or less, or about 1 angstrom. In certain cases, the distance between the flavin cofactor of the catalytic complex and the graphene layer is in the range of about 1 angstrom to about 5 angstroms, about 1 angstrom to about 10 angstroms, about 1 angstrom to about 20 angstroms, about 1 angstrom to about 50 angstroms, or about 1 angstrom to about 100 angstroms.

In some embodiments, the system comprises a first reservoir and a second reservoir. The first and second reservoirs may be separated from each other by a layer (e.g., a graphene layer). The first and second reservoirs may be positioned in any configuration. For example, the first and second reservoirs may be positioned side by side. In some embodiments, the first and second reservoirs may be positioned such that the first reservoir is on top of the second reservoir or the second reservoir is on top of the first reservoir. The first and second reservoirs may be configured such that the sole means of fluid communication between the first and second reservoirs is through the layer separating the two reservoirs. In some embodiments, the first and/or second reservoir is fluidly connected to at least one other conduit and/or reservoir. For example, the first reservoir may be in fluid communication with a source of water, a water outlet, an oxygen gas outlet, and/or a fuel cell employing oxygen gas. In some embodiments, the second reservoir may be in fluid communication with a hydrogen gas outlet and/or a fuel cell employing hydrogen gas. In some embodiments, the first reservoir and/or second reservoir comprise water, an ionic liquid, a hydrogel, and/or a sol-gel.

Some embodiments are directed to a system comprising one or more layers comprising graphene. As used herein, the term "graphene" is given its ordinary meaning in the art and generally refers to a single atomic layer of carbon atoms that are covalently bound to each other. The covalently-bound carbon atoms form repeating units that generally comprise 6-membered rings, but can also form 5-membered rings and/or 7-membered rings. Accordingly, it appears as if the covalently-bound carbon atoms (e.g., $sp^2$ carbon atoms) of graphene form a single layer having a basal plane comprising a fused network of aromatic rings. Graphene typically includes at least one basal plane containing interior carbon atoms of the fused network and a perimeter or edge containing the terminal carbon atoms of the fused network. Generally, the side ends or edges of the graphene are saturated with hydrogen atoms. However, the graphene material may contain non-carbon atoms at its edges.

It should be noted that graphene typically has a number of unique properties that can be advantageous. For example, graphene generally has high electron mobility at room temperature. In some cases, a graphene layer has an electron mobility of at least about 10,000 $cm^2 \cdot V^{-1} \cdot s^{-1}$, at least about 15,000 $cm^2 \cdot V^{-1} \cdot s^{-1}$, at least about 20,000 $cm^2 \cdot V^{-1} \cdot s^{-1}$, or at least about 100,000 $cm^2 \cdot V^{-1} \cdot s^{-1}$. Additionally, graphene generally has an energy band structure with a zero band gap.

One or more layers of graphene may be synthesized according to any method known at the art. For example, one or more graphene layers may be mechanically exfoliated or grown via chemical vapor deposition (CVD). In some cases, the graphene is monocrystalline. In some cases, the graphene is polycrystalline. It may be advantageous, in certain cases, for a graphene layer to be monocrystalline. For example, polycrystalline graphene may contain a greater density of defects due at least in part to the prevalence of grain boundaries. In some cases, a system may comprise a single layer of graphene. In some embodiments, a system comprises multiple layers of graphene (e.g., two layers, three layers, four layers, five layers, six layers, seven layers, or more).

In some embodiments, a first surface and/or a second surface of a graphene layer is substantially hydrophobic. The hydrophobicity or hydrophilicity of a surface may be determined using techniques known to those of ordinary skill in the art, such as contact angle measurements with water or the like. For example, a substantially hydrophobic surface may be one in which water forms a contact angle of greater than about 60° C. In certain embodiments, a substantially hydrophobic surface may advantageously facilitate coupling of a light-absorbing complex and/or a catalytic complex to the surface of the graphene layer.

In some embodiments, a first surface and/or a second surface of a graphene layer is substantially hydrophilic. A substantially hydrophilic surface may be one in which water forms a contact angle of less than about 60° C. In certain embodiments, a substantially hydrophilic surface may advantageously facilitate coupling of a light-absorbing complex and/or a catalytic complex to the surface of the graphene layer.

In some embodiments, the hydrophobicity of a first surface and/or a second surface of a graphene layer may be influenced by one or more substrate layers (e.g., a substrate layer directly adjacent the graphene layer). For example, in a particular, non-limiting embodiment, a system may comprise a first substrate layer (e.g., silicon), a second substrate layer comprising silicon dioxide, a third substrate layer comprising OTS, and a graphene layer directly adjacent the third substrate layer. In such an embodiment, the substrate layers may cause a surface (e.g., a second surface) of the graphene layer to be substantially hydrophobic.

In some embodiments, one or more graphene layers has a plurality of holes. The holes may have any shape. For example, the holes may be shaped as circles, ellipses, triangles, squares, rectangles, pentagons, hexagons, heptagons, octagons, stars, any regular or non-regular shapes, or any combination thereof. In some embodiments, each hole of the plurality of holes has a largest dimension (e.g., diameter) that is sufficiently small that a hydrogen ion ($H^+$) can pass through the hole, but a diatomic oxygen gas molecule and/or a diatomic hydrogen gas molecule cannot pass through the hole. In some embodiments, the average largest dimension (e.g., diameter) of the plurality of holes is at least about 0.1 nm, at least about 0.2 nm, at least about 0.5 nm, at least about 1 nm, at least about 2 nm, at least about 5 nm, at least about 10 nm, at least about 20 nm, at least about 50 nm, at least about 100 nm, at least about 500 nm, at least about 1 micron, at least about 2 microns, or at least about 5 microns. In some embodiments, the average largest dimension (e.g., diameter) of the plurality of holes is about 5 microns or less, about 2 microns or less, about 1 micron or less, about 500 nm or less, about 100 nm or less, about 50 nm or less, about 20 nm or less, about 10 nm or less, about 5 nm or less, about 2 nm or less, about 1 nm or less, about 0.5 nm or less, about 0.2 nm or less, or about 0.1 nm or less. In some embodiments, the average largest dimension (e.g., diameter) of the plurality of holes is in the range of about 0.1 nm to about 0.2 nm, about 0.1 nm to about 0.5 nm, about 0.1 nm to about 1 nm, about 0.1 nm to about 5 nm, about 0.1 nm to about 10 nm, about 0.1 nm to about 20 nm, about 0.1 nm to about 50 nm, about 0.1 nm to about 100 nm, about 0.1 nm to about 500 nm, about 0.1 nm to about 1 micron, about 0.1 nm to about 2 microns, about 0.1 nm to about 5 microns, about 0.2 nm to about 0.5 nm, about 0.2 nm to about 1 nm, about 0.2 nm to about 5 nm, about 0.2 nm to about 10 nm, about 0.5 nm to about 1 nm, about 0.5 nm to about 5 nm, about 0.5 nm to about 10 nm, about 1 nm to about 5 nm, about 1 nm to about 10 nm, about 1 nm to about 20 nm, about 1 nm to about 50 nm, about 1 nm to about 100 nm, about 1 nm to about 500 nm, about 1 nm to about 1 micron, about 1 nm to about 2 microns, about 1 nm to about 5 microns, about 5 nm to about 10 nm, about 10 nm to about 20 nm, about 10 nm to about 50 nm, about 10 nm to about 100 nm, about 10 nm to about 500 nm, about 10 nm to about 1 micron, about 10 nm to about 2 microns, about 10 nm to about 5 microns, about 50 nm to about 100 nm, about 50 nm to about 500 nm, about 50 nm to about 1 micron, about 50 nm to about 2 microns, about 50 nm to about 5 microns, about 100 nm to about 500 nm, about 100 nm to about 1 micron, about 100 nm to about 2 microns, about 100 nm to about 5 microns, or about 1 micron to about 5 microns. In some embodiments, a voltage may be applied across the one or more graphene layers to conduct hydrogen ions through the holes. For example, a voltage may be applied across a first electrode in solution in a first reservoir and a second electrode in solution in a second reservoir. In some cases, a voltage may be applied across silicon and an electrode in solution in a reservoir, where the electrode is not in the same reservoir as the silicon substrate layer. For example, if a silicon substrate layer is located in a first reservoir, the electrode may be located in a second reservoir. In some embodiments, hydrogen ions may diffuse through the holes (e.g., by an electrochemical potential).

In some embodiments, one or more graphene layers is fully extended (e.g., suspended) across one or more apertures in one or more substrate layers. An aperture may have any shape. For example, an aperture may be shaped as a circle, an ellipse, a triangle, a square, a rectangle, a pentagon, a hexagon, a heptagon, an octagon, a star, any regular or non-regular shape, or any combination thereof. In some embodiments, an aperture has a largest dimension (e.g., diameter, length) of at least about 100 nm, at least about 500 nm, at least about 1 micron, at least about 2 microns, at least about 5 microns, at least about 10 microns, at least about 15 microns, at least about 20 microns, at least about 25 microns, at least about 30 microns, at least about 35 microns, and/or at least about 40 microns. In some embodiments, an aperture has a largest dimension of about 40 microns or less, about 35 microns or less, about 30 microns or less, about 25 microns or less, about 20 microns or less, about 15 microns or less, about 10 microns or less, about 5 microns or less, about 2 microns or less, about 1 micron or less, about 500 nm or less, or about 100 nm or less. In some embodiments, an aperture has a largest dimension in the range of about 100 nm to about 500 nm, about 100 nm to about 1 micron, about 100 nm to about 5 microns, about 100 nm to about 10 microns, about 100 nm to about 20 microns, about 100 nm to about 30 microns, about 100 nm to about 40 microns, about 1 micron to about 5 microns, about 1 micron to about 10 microns, about 1 micron to about 20 microns, about 1 micron to about 30 microns, about 1 micron to about 40 microns, about 5 microns to about 10 microns, about 5 microns to about 20 microns, about 5 microns to about 30 microns, about 5 microns to about 40 microns, about 10 microns to about 20 microns, about 10 microns to about 30 microns, about 10 microns to about 40 microns, about 15 microns to about 20 microns, about 15 microns to about 30 microns, about 15 microns to about 40 microns, about 20 microns to about 30 microns, about 20 microns to about 40 microns, or about 30 microns to about 40 microns.

In some embodiments, one or more substrate layers have a plurality of apertures. The one or more substrate layers may have any number of apertures. In some embodiments, one or more substrate layers may have at least about 2 apertures, at least about 5 apertures, at least about 10 apertures, at least about 20 apertures, at least about 50 apertures, at least about 100 apertures, at least about 200 apertures, at least about 500 apertures, or at least about 1000 apertures. In some cases, one or more substrate layers may have about 1000 apertures or less, about 500 apertures or less, about 200 apertures or less, about 100 apertures or less, about 50 apertures or less, about 20 apertures or less, about 10 apertures or less, about 5 apertures or less, or about 2 apertures or less. In some embodiments, one or more substrate layers have a number of apertures in the range of about 2 apertures to about 10 apertures, about 2 apertures to about 20 apertures, about 2 apertures to about 50 apertures, about 2 apertures to about 100 apertures, about 2 apertures to about 200 apertures, about 2 apertures to about 500 apertures, about 2 apertures to about 1000 apertures, about 10 apertures to about 20 apertures, about 10 apertures to about 50 apertures, about 10 apertures to about 100 apertures, about 10 apertures to about 200 apertures, about 10 apertures to about 500 apertures, about 10 apertures to about 1000 apertures, about 50 apertures to about 100 apertures, about 50 apertures to about 200 apertures, about 50 apertures to about 500 apertures, about 50 apertures to about 1000 apertures, about 100 apertures to about 200 apertures, about 100 apertures to about 500 apertures, about 100 apertures to about 1000 apertures, about 200 apertures to about 500 apertures, about 200 apertures to about 1000 apertures, or about 500 apertures to about 1000 apertures. In some embodiments, the apertures may be arranged in an array (e.g., a regular array, a geometric array). In some embodiments, the apertures may be arranged according to a pattern. In some embodiments, the apertures may be irregularly arranged. The apertures may be created in one or more substrate layers according to any method known in the art. Non-limiting examples of suitable methods include photolithography, reactive ion etching (RIE), and KOH silicon etching.

In some embodiments, a graphene layer is suspended over an aperture in an optional first substrate layer. In certain cases, the first substrate layer comprises an electrically insulating material. Examples of suitable electrically insulating materials include, but are not limited to, silicon dioxide (e.g., quartz, fused silica), silicon nitride, hexagonal boron nitride, aluminum oxide (e.g., sapphire), and combinations thereof. In some embodiments, the first substrate layer is an electrically insulating layer. According to some embodiments, the first substrate layer comprises an electrically conductive material. The electrically conductive material may, for example, comprise a metal and/or a semiconductor. Non-limiting examples of suitable semiconductors include silicon, germanium, gallium nitride, gallium phosphide, gallium arsenide, indium gallium arsenide, and combinations thereof. Non-limiting examples of suitable metals include copper, aluminum, silver, gold, platinum, nickel, and combinations thereof. In some embodiments, the first substrate layer is an electrically conductive layer. In some embodiments, a first substrate layer comprises silicon (e.g., a silicon wafer). In certain cases, the first substrate layer (e.g., comprising silicon) has a thickness of at least about 100 microns, at least about 500 microns, at least about 1000 microns, at least about 0.5 cm, at least about 1 cm, at least about 2 cm, at least about 5 cm, or at least about 10 cm. In some embodiments, the first substrate layer has a thickness of about 10 cm or less, about 5 cm or less, about 2 cm or less, about 1 cm or less, about 0.5 cm or less, about 1000 microns or less, about 500 microns or less, or about 100 microns or less. In some embodiments, the first substrate layer has a thickness in the range of about 500 microns to about 1000 microns, about 500 microns to about 0.5 cm, about 500 microns to about 1 cm, about 500 microns to about 2 cm, about 500 microns to about 5 cm, about 500 microns to about 10 cm, about 1 cm to about 2 cm, about 1 cm to about 5 cm, about 1 cm to about 10 cm, about 2 cm to about 10 cm, or about 5 cm to about 10 cm. In certain embodiments, at least a portion of the first substrate layer is directly adjacent the graphene layer. In some embodiments, one or more intervening layers are positioned between the first substrate layer and the graphene layer.

In some embodiments, a graphene layer is suspended over an aperture in an optional second substrate layer and/or an optional third substrate layer. In some embodiments, the second and/or third substrate layer is electrically insulating. In some embodiments, the second and/or third substrate layer comprises an electrically insulating material. Examples of suitable electrically insulating materials include, but are not limited to, silicon dioxide (e.g., quartz, fused silica), silicon nitride, hexagonal boron nitride, OTS, aluminum oxide (e.g., sapphire), and combinations thereof. In some embodiments, the second and/or third substrate layer is electrically conductive. In some cases, the second and/or third substrate layer comprises an electrically conductive material. The electrically conductive material may, for example, comprise a metal and/or a semiconductor. Non-limiting examples of suitable semiconductors include silicon, germanium, gallium nitride, gallium phosphide, gallium arsenide, indium gallium arsenide, and combinations thereof. Non-limiting examples of suitable metals include copper, aluminum, silver, gold, platinum, nickel, and combinations thereof. The second and/or third substrate layer may, in some cases, be hydrophilic and/or hydrophobic. In some embodiments, the second and/or third substrate layer (e.g., comprising silicon dioxide and/or OTS) promotes adhesion between a substrate layer (e.g., the first substrate layer, the second substrate layer) and a graphene layer. In certain embodiments, at least a portion of the second substrate layer and/or third substrate layer is directly adjacent the graphene layer. In some embodiments, one or more intervening layers are positioned between the graphene layer and the second substrate layer and/or third substrate layer.

In some embodiments, the second and/or third substrate layer has a thickness of at least about 10 nm, at least about 20 nm, at least about 50 nm, at least about 100 nm, at least about 200 nm, at least about 300 nm, at least about 400 nm, at least about 500 nm, or at least about 1 micron. In some embodiments, the second and/or third substrate layer has a thickness of about 1 micron or less, about 500 nm or less, about 400 nm or less, about 300 nm or less, about 200 nm or less, about 100 nm or less, about 50 nm or less, about 20 nm or less, or about 10 nm or less. In some embodiments, the second and/or third substrate layer has a thickness in the range of about 10 nm to about 20 nm, about 10 nm to about 50 nm, about 10 nm to about 100 nm, about 10 nm to about 200 nm, about 10 nm to about 300 nm, about 10 nm to about 500 nm, about 10 nm to about 1 micron, about 50 nm to about 100 nm, about 50 nm to about 200 nm, about 50 nm to about 300 nm, about 50 nm to about 500 nm, about 50 nm to about 1 micron, about 100 nm to about 300 nm, about 100 nm to about 500 nm, or about 100 nm to about 1 micron.

In some cases, first substrate layer, second substrate layer, and/or third substrate layer are substantially transparent to at least a portion of electromagnetic radiation (e.g., visible light). Non-limiting examples of suitable transparent materials include quartz and silicon nitride. It may be advantageous for certain embodiments to comprise one or more transparent substrate layers, as such embodiments may result in more light being absorbed by one or more light-absorbing complexes coupled to a graphene layer.

In some embodiments, one or more graphene layers is transferred to one or more substrate layers. Any method of transferring known in the art may be used. In some embodiments, a wet transfer method is used. The wet transfer method may, in some cases, comprise a critical point drying step. The critical point drawing step may advantageously reduce surface tension across a suspended graphene layer. In some embodiments, a dry transfer method is used.

Systems described herein comprise a graphene layer, which has a redox potential (e.g., a measure of the tendency of the graphene layer to gain or lose electrons). In certain embodiments, the redox potential of the graphene layer may be varied. For example, in some embodiments, the graphene layer is in electrical communication with a battery and/or potentiostat that is also in electrical communication with a reference electrode (e.g., an electrode with a stable, well-known potential). Non-limiting examples of suitable reference electrodes include a silver chloride (e.g., Ag/AgCl) electrode and a platinum electrode. The reference electrode generally is immersed in a solution comprising a salt. A non-limiting example of a suitable salt is potassium chloride (KCl). Examples of suitable solvents and/or hosts for the salt solution include, but are not limited to, water, ionic liquids, hydrogels, and/or sol-gels. In some cases, the graphene layer is in ionic communication with the salt solution of the reference electrode. For example, a salt bridge may be positioned between the salt solution of the reference electrode and a first reservoir (e.g., reservoir 102 in FIG. 1A) and/or second reservoir (e.g., reservoir 104 in FIG. 1A) of the graphene-layer-comprising system. In some cases, varying the voltage of the battery and/or potentiostat may cause the redox potential of the graphene layer to be varied. It may be advantageous, in certain cases, for the redox potential of the graphene layer to be adjusted to have a certain value relative to the redox potential of a portion of a light-absorbing complex (e.g., PQ-A of PSII) and/or relative to a portion of a catalytic complex (e.g., a flavin cofactor of FNR) coupled to the graphene layer.

In some embodiments, a voltage (e.g., a back gate voltage) may be applied between a graphene layer and a conductive substrate layer (e.g., a substrate layer comprising silicon). In some embodiments, a voltage (e.g., a top gate voltage) may be applied between a graphene layer and an electrode positioned in the first reservoir and/or the second reservoir. Non-limiting examples of suitable electrodes include a silver chloride (Ag/AgCl) electrode and a platinum electrode. Due to the unique band structure of graphene, graphene generally has a density of levels that is at or about zero at the charge neutrality point. The density of states of a graphene layer can therefore be easily adjusted by a back gate voltage and/or a top gate voltage. In some embodiments, the density of states can control whether an electron is transferred to graphene (e.g., from the light-absorbing complex), whether an electron is transferred from graphene (e.g., to the catalytic complex), and/or whether electron transfer can occur across graphene (e.g., from the light-absorbing complex to the catalytic complex). In some cases, the density of states can control the rate of electron transfer to graphene (e.g., from the light-absorbing complex) and/or the rate of electron transfer from graphene (e.g., to the catalytic complex). In some embodiments, the applied back gate voltage and/or applied top gate voltage is at least about 1 V, at least about 5 V, at least about 10 V, at least about 20 V, at least about 50 V, at least about 100 V, at least about 150 V, at least about 200 V, or at least about 500 V. In some embodiments, the applied back gate voltage and/or applied top gate voltage is about 500 V or less, about 200 V or less, about 150 V or less, about 100 V or less, about 50 V or less, about 20 V or less, about 10 V or less, about 5 V or less, or about 1 V or less. In some embodiments, the applied back gate voltage and/or applied top gate voltage is in the range from about 1 V to about 10 V, about 1 V to about 20 V, about 1 V to about 50 V, about 1 V to about 100 V, about 1 V to about 200 V, about 1 V to about 500 V, about 10 V to about 50 V, about 10 V to about 100 V, about 10 V to about 200 V, about 10 V to about 500 V, about 50 V to about 100 V, about 50 V to about 200 V, about 50 V to about 500 V, about 100 V to about 200 V, about 100 V to about 500 V, or about 200 V to about 500 V. In some embodiments, the applied back gate voltage and/or top gate voltage may result in the Fermi level of the graphene layer changing (e.g., up or down relative to the charge neutrality point) by at least about 0.1 V, at least about 0.2 V, at least about 0.5 V, at least about 1 V, at least about 2 V, at least about 5 V, or at least about 10 V. In some cases, the change in the Fermi level of the graphene layer is in the range of about 0.1 V to about 0.5 V, about 0.1 V to about 1 V, about 0.1 V to about 2 V, about 0.1 V to about 5 V, about 0.1 V to about 10 V, about 0.5 V to about 1 V, about 0.5 V to about 2 V, about 0.5 V to about 5 V, about 0.5 V to about 10 V, or about 1 V to about 10 V. When the Fermi level changes relative to the charge neutrality point, the density of states generally changes. In certain embodiments, the system may form a field-effect transistor (FET). In some embodiments, a graphene layer may act as a channel of the FET. In certain cases, a conductive substrate layer (e.g., a silicon substrate layer) may act as a gate electrode of the FET.

It should be noted that a top gate voltage and/or a back gate voltage may be applied to a graphene layer that is in electrical communication with a battery and/or potentiostat that is also in electrical communication with a reference electrode immersed in a salt solution. The graphene layer may also be in ionic communication with the salt solution (e.g., via a salt bridge). Accordingly, in some embodiments, the redox potential of the graphene layer may be varied by changing the voltage of the battery and/or potentiostat in electrical communication with the reference electrode, and the density of states of the graphene layer may be varied by changing the value of the applied top gate voltage and/or back gate voltage.

Some embodiments are directed to methods. In some embodiments, a method comprises the step of providing a system described herein. In certain embodiments, the method further comprises the step of exposing at least a portion of the system (e.g., a first surface of a graphene layer and/or a second surface of a graphene layer, or a first reservoir and/or a second reservoir) to light. In some cases, the light may be visible light. In certain embodiments, the light may be sunlight. In some cases, the method further comprises exposing at least a portion of the system (e.g., a first surface of a graphene layer and/or a second surface of a graphene layer, or a first reservoir and/or a second reservoir) to water. The method may also comprise applying a voltage to a layer comprising graphene. In certain embodiments, the voltage modulates the redox potential of the layer comprising graphene. In some cases, the method comprises applying a voltage between the layer comprising graphene and a substrate layer comprising an electrically conductive material (e.g., a first substrate layer comprising silicon). In certain cases, the method comprises applying a voltage between the layer comprising graphene and an electrode (e.g., an electrode positioned in a first reservoir and/or a second reservoir). The applied voltage may modulate transfer of one or more electrons to the layer comprising graphene (e.g., from a light-absorbing complex to the layer comprising graphene) and/or may modulate transfer of one or more electrons from the layer comprising graphene (e.g., from the layer comprising graphene to a catalytic complex). In some cases, the voltage may modulate transfer of one or more electrons across the layer comprising graphene (e.g., from a light-absorbing complex coupled to one surface of the graphene layer to a catalytic complex coupled to another surface of the graphene layer).

The following examples are intended to illustrate certain embodiments of the present invention, but do not exemplify the full scope of the invention.

Example 1

This example describes improved graphene (Gr) synthesis and transfer methods for suspending large (about 0.75 mm to about 1.5 mm diameter), single crystals of pristine, CVD-grown Gr over 5-30 micron (μm) diameter apertures in a $SiO_2/Si_3N_4$ substrate. Due to the improved Gr synthesis and transfer methods, high yields (about 10-60%) were achieved. In addition to suspending monolayer Gr, it was found that single crystals of bi- and trilayer Gr could also be suspended. Optical microscopy and Raman spectroscopy were used to determine the presence and number of suspended Gr layers, and electron diffraction (ED) was used to confirm that the Gr was monocrystalline. Raman spectroscopy was also used to classify the relative stacking orientation between the individual monolayers in suspended multilayer crystals. It is believed that this work represents the largest suspended areas (about 700 μm$^2$) of pristine single crystals of intact and chemically unmodified, mono- and multilayer Gr on insulating substrates achieved to date and that it will be of significant benefit to future Gr studies and applications.

Since the discovery of a facile method for isolating graphene (Gr) from bulk graphite, graphene's fascinating properties have generated much interest both in the fundamental physics describing its unique behavior as well as in its potential applications as a highly conductive, two-dimensional material. In addition to its outstanding electrical characteristics, Gr is the strongest material ever measured. Despite its intrinsic mechanical strength, large areas of Gr have commonly been studied while being supported by another material. This is due in part to graphene's atomic thinness and its inherent lattice defects that leave it vulnerable to macroscopic tearing and rupturing. Additionally, although Gr is rigid on a molecular scale, it is pliable on the micron length scale and is prone to folding and rolling up upon itself. Despite these difficulties, certain studies require freestanding Gr because of the reduced charge carrier mobility and the undesired doping that substrates induce. As a result, suspended Gr has become an important experimental system for not only studying graphene's fundamental properties, but also for pursuing many of its electronic and nanomechanical applications. Such applications include using Gr as an electromechanical resonator, a surface plasmon wave guide medium, a desalination filter, a TEM imaging membrane, a NEMS switch, and a DNA sequencing nanopore, among others.

Although mechanically exfoliated Gr may be less defective than chemical vapor deposition (CVD) grown Gr, and hence may be less prone to tearing while unsupported, only small areas (about 100 μm$^2$) of it were routinely achievable, thus limiting parallel and scalable device fabrication. Large areas of polycrystalline CVD Gr, however, could be easily synthesized. Due in part to the prevalence of grain boundaries, polycrystalline CVD Gr contains greater defect densities that weaken suspended Gr membranes and are likely to reduce suspension yields. With the help of recent advances in the synthesis of large grains (about 1 mm in diameter) of CVD Gr, it was demonstrated that it is possible to create scalable, suspended-Gr devices, in parallel, over apertures greater than about 10 μm in diameter on silicon-based, insulating support substrates. Optical microscopy, Raman spectroscopy, and electron diffraction (ED) were used to demonstrate that single, large grains (about 0.75-1.5 mm diameter) of Gr, as part of a continuous, polycrystalline Gr sheet, could be suspended with yields between about 10-60% over apertures in a $SiO_2/Si_3N_4$ substrate ranging in diameter from 5-30 μm (about 20-700 μm$^2$). It was demonstrated that both wet and dry Gr transfer methods could be used to create the large-area suspended-Gr devices and that the different transfer methods resulted in roughly similar device yields. Furthermore, because the large-grain CVD synthesis protocol that was developed resulted in the formation of areas containing multilayer Gr crystals, it was shown that individual crystals of bi- and trilayer Gr could be suspended over large apertures. It is believed that this work represents the largest suspended areas (about 700 μm$^2$) of pristine single crystals of intact and chemically unmodified, mono- and multilayer Gr on insulating substrates achieved to date.

Fabrication of suspended-Gr devices began with the synthesis of continuous sheets of large-grain, polycrystalline Gr grown on 25-μm thick copper foils using a home-built low-pressure CVD system. Briefly, a 2×7 cm$^2$ area of Cu foil (99.8% pure) was first annealed under an atmosphere of Ar (300 sccm) for 5 min. at T=1070° C. and P~750 mTorr. Graphene synthesis was then begun by simultaneously introducing $H_2$ and diluted $CH_4$ (500 ppm in a balance of Ar), each at a flow rate of 20 sccm, and by changing the Ar flow rate to 310 sccm. The pressure and temperature were held constant at about 750 mTorr and 1070° C., and the reaction was run for 200 min. before it was stopped by the rapid cooling of the system with an external fan.

FIGS. 2A-D show SEM images of groups of hexagonal Gr grains on Cu taken after (A) 30 minutes, (B) 60 minutes, (C) 120 minutes, and (D) 180 minutes of synthesis. After 30 min, the majority of grains reached a diameter of about 0.3-0.6 mm, and fewer than 10% of the grains examined had yet to grow into other grains. By 60 min, most grains were greater than 1 mm and had started to merge with adjacent grains. After 180 min, Gr covered most of the Cu foil, and large Gr islands consisting of individual grains that were between about 2 mm to 3.5 mm were common. Allowing the reaction to run for 200 min. gave a continuous sheet of Gr. The average grain diameter in the final polycrystalline sheet was estimated to be about 0.75 mm to about 1.5 mm.

Figure 3A:
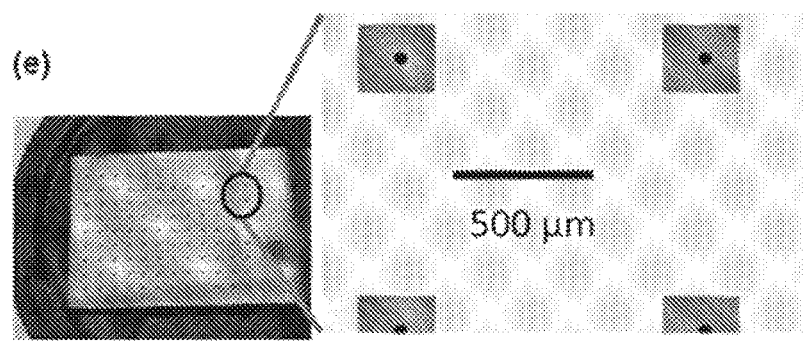
FIG. 3A shows an optical microscope image of a substrate, according to some embodiments.

The supporting, silicon-based substrate was fabricated by creating 9×12 arrays of circular apertures in a 4" silicon wafer with a 300-nm thick capping layer of low-stress $Si_3N_4$. Standard photolithography, reactive ion etch (RIE), and KOH silicon etch protocols were used to first create freestanding $Si_3N_4$ membranes and then to create apertures in those membranes. Finally, a 300-nm thick layer of $SiO_2$ was deposited on top of the $Si_3N_4$ to promote Gr adhesion and to allow for the visualization of the Gr on the substrate. FIG. 3A shows an optical image of an array of 108 apertures before $SiO_2$ deposition. Each of the apertures was centered on a freestanding $Si_3N_4$ membrane (the $Si_3N_4$ membranes are the squares and the apertures are the circles in the expanded image).

Figure 3B:
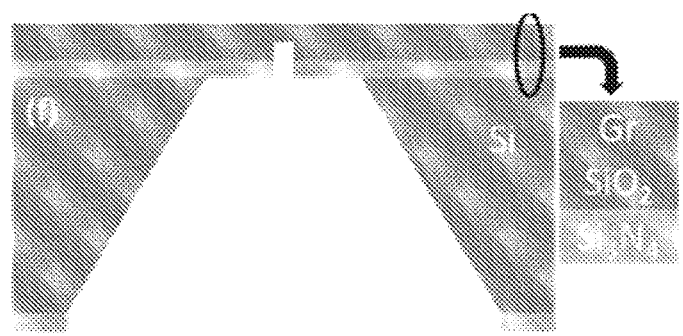
FIG. 3B shows a cross-sectional schematic illustration of a suspended graphene device, according to some embodiments.

Devices were created by transferring Gr from the Cu foil to the aperture-containing substrate. In order to assess the effect of the transfer method on the suspension yield, as well as to enhance the applicability of our fabrication methods, wet and dry Gr transfer methods were each separately developed and optimized. The wet transfer method that was developed was modified to contain a final critical point drying (CPD) step to reduce the surface tension across suspended Gr membranes. The dry transfer method that was developed was modified to improve Gr adhesion to the substrate by reducing the thickness of the polymethyl methacrylate (PMMA) support layer and by softening the PMMA layer using an acetone vapor humidor prior to thermal PMMA removal. The dry transfer method was further modified to increase the area of Gr that could be transferred per transfer attempt. The dry transfer method was of interest because it allowed Gr to be transferred to hydrophobic substrates, to substrates that were incompatible with $H_2O$, and to substrates containing wells or cavities without trapping pockets of $H_2O$. FIG. 3B illustrates a single suspended-Gr device upon completion of the fabrication process. A complete description of the Gr synthesis, substrate fabrication, and Gr transfer methods is provided in Example 2.

Results from both optical microscopy and Raman spectroscopy analysis of successfully suspended Gr are shown in FIG. 4. FIG. 4A is a grayscale optical image of Gr suspended over a 30-μm aperture using the wet transfer method. Inside the aperture, the lack of contrast indicated the suspended area was free of tears, particles, large areas of residual polymer contamination, and multiple Gr layers. A single Raman spectrum taken at the center of the aperture is shown in FIG. 4B. All Raman data were taken with a laser excitation photon energy of 2.33 eV at 8 mW and a laser spot size of about 1-2 μm. The shape, spectral position, and relative intensity of the G and G' peaks indicated that the Gr was monolayer. The D peak was nearly absent, confirming that the Gr was pristine with very few defects. For further confirmation of the uniformity of monolayer Gr over the entire aperture, a Raman area scan was taken. FIG. 4C shows the resulting map of the Raman shift of the G' peak. Inside the aperture, the Raman shift was fairly constant and was centered at about 2665 $cm^{-1}$. Outside the aperture, the presence of the supporting $SiO_2/Si_3N_4$ substrate caused the G' peak to mostly blue shift to about 2675-2680 $cm^{-1}$, although small regions of red shifting were also observed. These results were typical for most of the devices that were made.

Figure 4A:
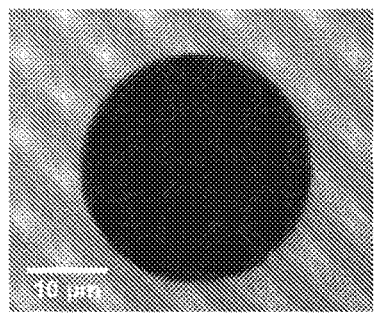
FIG. 4A shows an optical microscope image of freestanding, monolayer graphene over a 30-micron-diameter aperture, according to some embodiments.
Figure 4B:
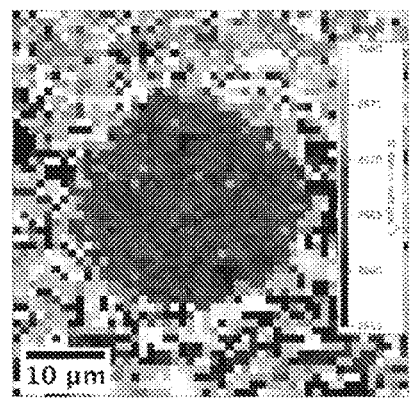
FIG. 4B shows a spatial Raman map of a suspended graphene device, according to some embodiments.
Figure 4C:
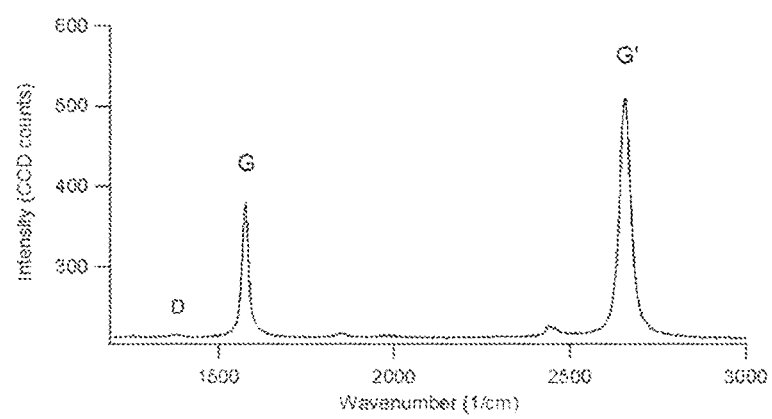
FIG. 4C shows a Raman point spectrum taken at the center of an aperture of a suspended graphene device, according to some embodiments.
Figure 4D:
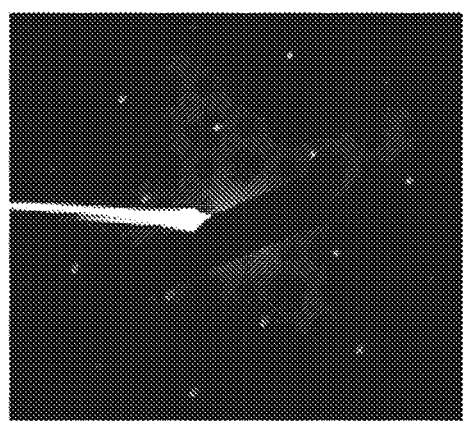
FIG. 4D shows an electron diffraction pattern of a 10-micron-diameter suspended monolayer graphene device, according to some embodiments.

In addition to the suspended-Gr devices having uniform, monolayer Gr, it was assumed that they were very likely monocrystalline because the area of the average Gr crystal in the polycrystalline sheet was at least 103 times larger than the area of the largest aperture. This assumption was confirmed using electron diffraction (ED). FIG. 4D shows the electron diffraction pattern of monolayer Gr suspended over a 10-μm aperture. The diffraction pattern was taken at low magnification with an about 5-μm diameter beam spot size and an acceleration voltage of 200 kV. The diffraction pattern indicated that the suspended Gr was indeed monocrystalline because only one set of hexagonal spots with constant intensity was observed. Additionally, it showed that the Gr was pristine because the spots were clear, with only a small amount of amorphous diffraction from contaminants and adsorbates.

Figure 4E:
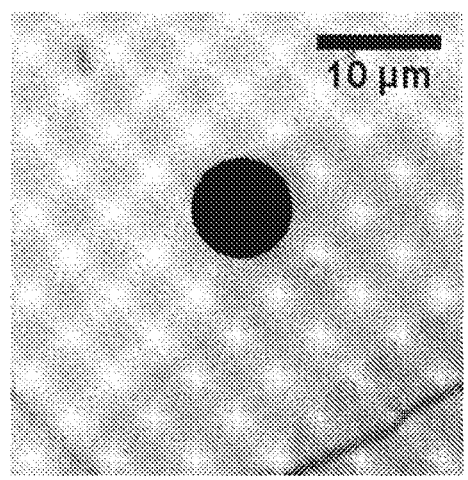
FIG. 4E shows an optical microscope image of a 10-micron-diameter suspended graphene device bisected by the edge of a bilayer graphene crystal, according to some embodiments.
Figure 4F:
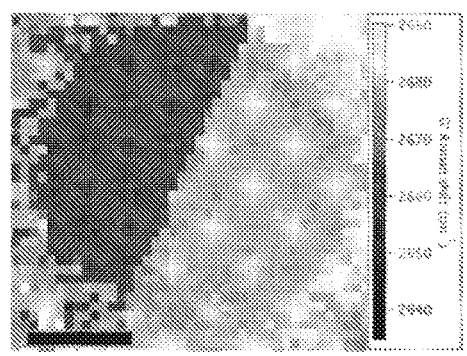
FIG. 4F shows a spatial Raman map of a bisected suspended graphene device, according to some embodiments.

With the CVD synthesis protocol, regions of multilayer Gr could also be formed, which allowed for the fabrication of suspended multilayer Gr devices. The size of the multilayer grains (about 50-200 μm) as well as the optical contrast difference on $SiO_2$ between areas with differing numbers of Gr layers allowed for facile identification of the layer number (up to about 5-6 layers) for such regions using optical microscopy. An example of a 10-μm aperture spanned by both mono- and bilayer Gr is provided in the grayscale optical microscope image of FIG. 2E. This device was created using the dry transfer method, and the number of layers was labeled as 1-L, 2-L, etc. FIG. 4E shows that the aperture was bisected by the edge of a bilayer Gr crystal, with the left half consisting of monolayer Gr and the right half of bilayer Gr. In the Raman map of FIG. 4F, which plots the Raman shift of the G' peak over the entire bisected aperture, a clear blue shift was seen when moving from the left monolayer region (about 2665 $cm^{-1}$) to the right bilayer region (about 2675-2680 $cm^{-1}$), as was expected.

Figure 5:
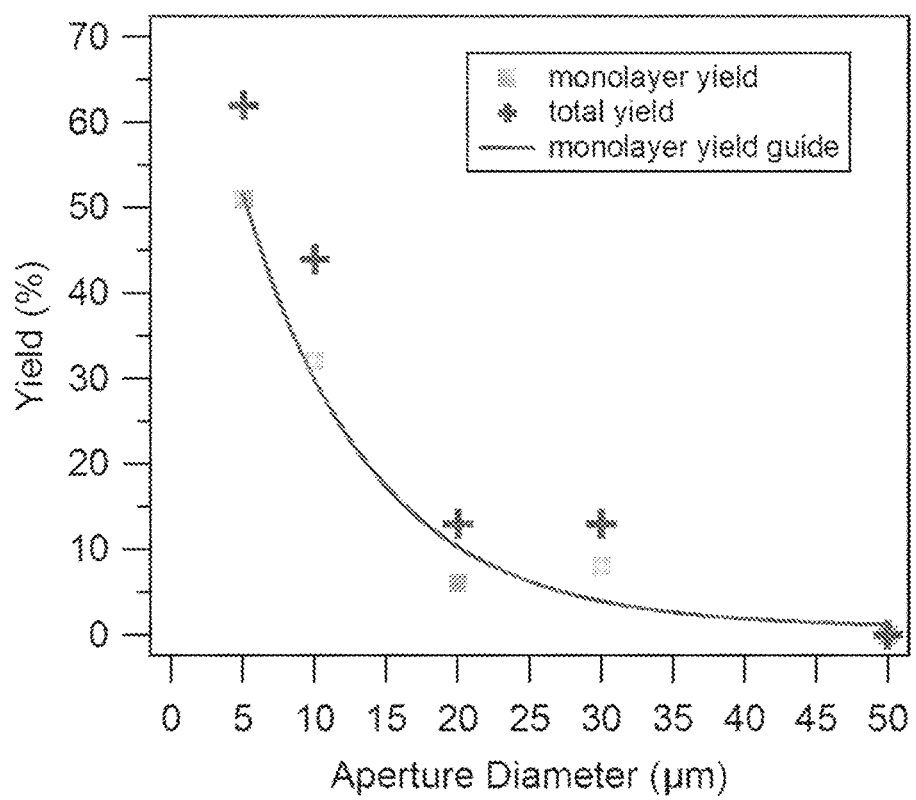
FIG. 5 shows a plot of fabrication yield as a function of aperture diameter, according to some embodiments.

FIG. 5 shows a plot of the suspension yield for the wet transfer method as a function of aperture diameter. Both optical microscopy and Raman spectroscopy were used to verify the presence and layer number of suspended Gr over each aperture. Gr suspension was attempted over apertures of 5, 10, 20, 30, and 50 μm in diameter. Because about 10-20% of the area of the continuous Gr sheets on Cu contained multilayer crystals, a distinction was made between total suspension yield, i.e. the total number of apertures with either suspended mono- or multilayer Gr, and monolayer suspension yield, i.e. the total number of apertures with only monolayer Gr. Total suspension yield decreased from 62% for 5-μm diameter apertures to 13% for 30-μm apertures. It was apparent from these yield data that as aperture diameter increased, the percentage of the total suspended Gr membranes that are multilayer tended to also increase. Despite variations in the amount of multilayer areas between each Gr sheet transferred, this trend suggested that multilayer membranes were more readily suspended over larger apertures than were monolayer membranes. It is important to note that the CPD step was an important step of the wet transfer method. The total yield for 10-μm diameter apertures decreased from 44% to about 7% if this step was omitted.

Due to the relative complexity of the dry transfer method, it was used only to suspend Gr over 10 and 30-μm diameter apertures. The total suspension yield for the dry transfer method for 10 and 30-μm apertures was 33% and 1%, respectively, whereas the monolayer suspension yield was 28% and 1%, respectively. Reducing the PMMA thickness and adding an acetone vapor PMMA softening step were determined to be important for successfully suspending Gr using this method, as Gr adhesion to the substrate was very poor otherwise. Although both wet and dry transfer methods gave somewhat similar yields for 10-μm apertures (44% for the wet transfer vs. 33% for the dry transfer), the wet transfer yield was more than an order of magnitude greater than the dry transfer yield for 30-μm apertures (13% vs. 1%). Overall, the wet transfer method produced consistently higher yields and was easier to implement than the dry transfer method. The results showed that key steps in each of the transfer processes could greatly affect the yield of suspended Gr devices, but that devices could nevertheless be successfully fabricated using either method. This robustness may be due to the intrinsic strength of large grain, monocrystalline Gr.

Figure 6:
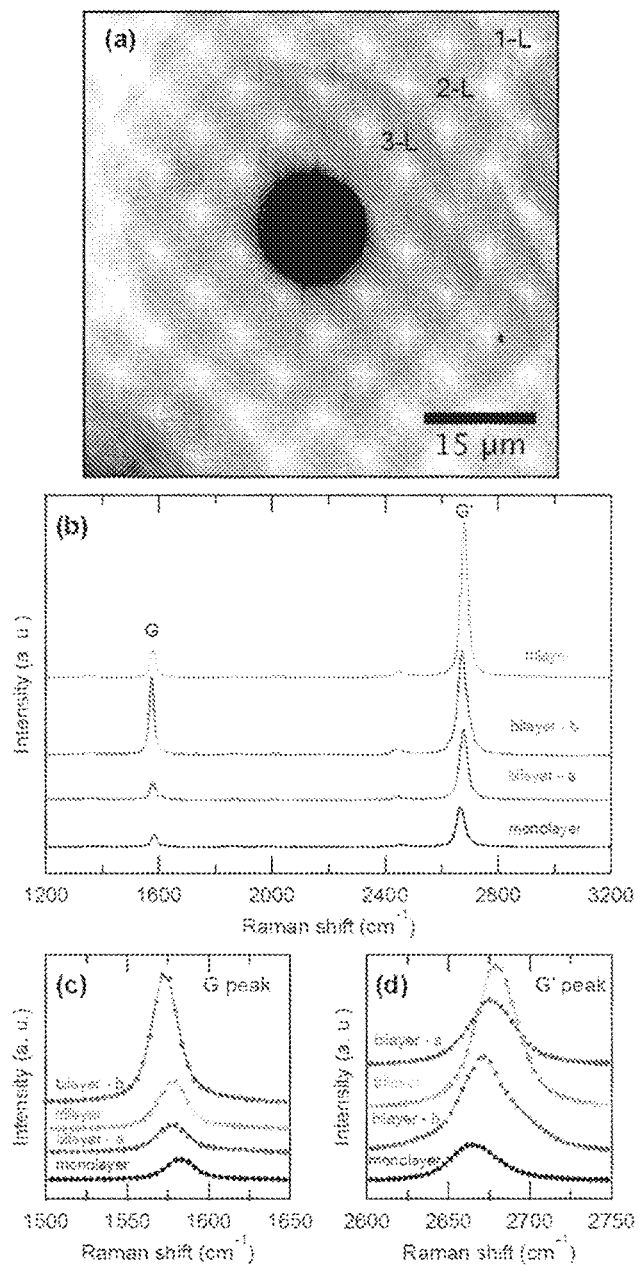
FIG. 6A shows an optical microscope image of trilayer graphene suspended over an about 10 micron aperture, according to some embodiments.
FIG. 6B-D show Raman point spectra for suspended mono-, bi-, and trilayer graphene, according to some embodiments.

Despite the presence of some multilayer grains containing more than 7 layers in the polycrystalline Gr sheets, suspended multilayer Gr devices with only bi- and trilayers were observed. FIG. 6A shows a typical grayscale optical microscope image of a trilayer region of Gr that completely spanned an about 10-μm aperture (the number of layers was labeled as 1-L, 2-L, etc.). A comparison of the Raman point spectra of suspended mono-, bi-, and trilayer Gr over separate 10-μm apertures was given in FIG. 6B. Traces labeled as 'bilayer-a' and 'bilayer-b' represented Raman spectra that were observed for two different and distinct bilayer devices. The differences in the bilayer spectra were possibly caused by differences in the stacking order of the bilayers, as CVD grown Gr often produced bilayers that were randomly rotationally disordered. The changes in the G and G' bands for the different Gr types are explicitly shown in FIGS. 6C and 6D, respectively. As expected, the energy and width of the G band changed only slightly for the different types of multilayers, with bilayer-b displaying the largest red shift compared to monolayer Gr. The G' band, however, showed appreciable blue shifting and a slight peak narrowing, except in the case of the bilayer-b trace which exhibits a broadening of the G' band.

Figure 7:
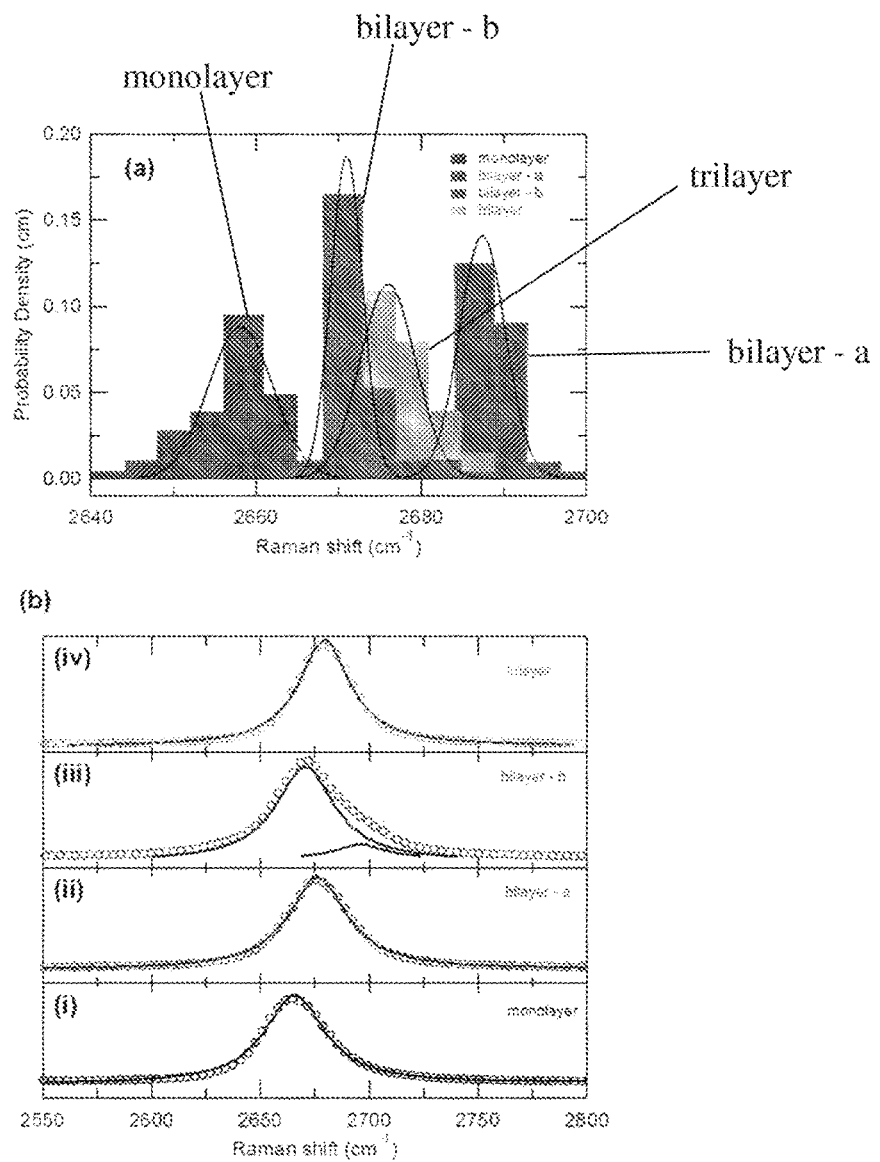
FIG. 7A shows density histograms showing the distribution of the G' Raman shift over the suspended region for various graphene devices, according to some embodiments.
FIG. 7B shows G' peak shape for monolayer, bilayer, and trilayer graphene devices, according to some embodiments.

To demonstrate the significance of the change in the G' band energy in identifying multilayer Gr, density histograms of the distribution of the G' band energy over the suspended Gr area for monolayer, bilayer-a, bilayer-b, and trilayer devices were plotted in FIG. 7A. Each histogram represented data from an individual 10-μm device and each has been fitted with a normal distribution. To exclude changes caused by the surrounding $SiO_2/Si_3N_4$ substrate, the histograms included only those scan points that were within a 4-μm radius of the center of the aperture. A clear separation was seen between the distributions for the monolayer and the multilayer Gr devices (Δω about 13-30 $cm^{-1}$), which allowed monolayer Gr to be readily distinguished from multilayer Gr. Because the magnitude of the G' blue shift for multilayer Gr depended on both the layer number and on the relative stacking orientation between the individual monolayers, however, neither the layer number nor the stacking orientation could be determined by the shift alone.

In addition to the change in energy of the G' band, the shape of the band can also provide information regarding the stacking order of multilayer Gr. FIG. 7B gives the results of a Lorentz distribution fit to the G' band for (i) monolayer, (ii) bilayer-a, (iii) bilayer-b, and (iv) trilayer devices. All the traces were best fitted with a single Lorentzian peak, except for the bilayer-b trace, which was fitted with two Lorentzian peaks. For each of these multilayer devices, this demonstrated that the multilayer Gr exhibited rotational misalignment between its individual monolayers. All of the suspended multilayer Gr devices that were examined showed this inter-layer rotational misalignment. Taken together, the shape of the G' peak, the change in energy of the G' band, and the optical micrographs allowed the identification of the number of Gr layers present in each device as well as the classification of the rotational order between the layers of multilayer devices.

In summary, it was demonstrated that large-area, suspended-Gr devices consisting of large, single grains of both pristine mono- and multilayer CVD-grown Gr could be fabricated with good yields using silicon-based, insulating support substrates, and that these devices could be fabricated in a parallel and scalable fashion. It was also shown that both wet and dry Gr transfer methods could be used to successfully suspend Gr with roughly similar yields, thus enhancing the applicability of the methods.

Example 2

This example describes the methods used to produce the suspended graphene devices of Example 1.

1. Substrate Fabrication

Figure 8:
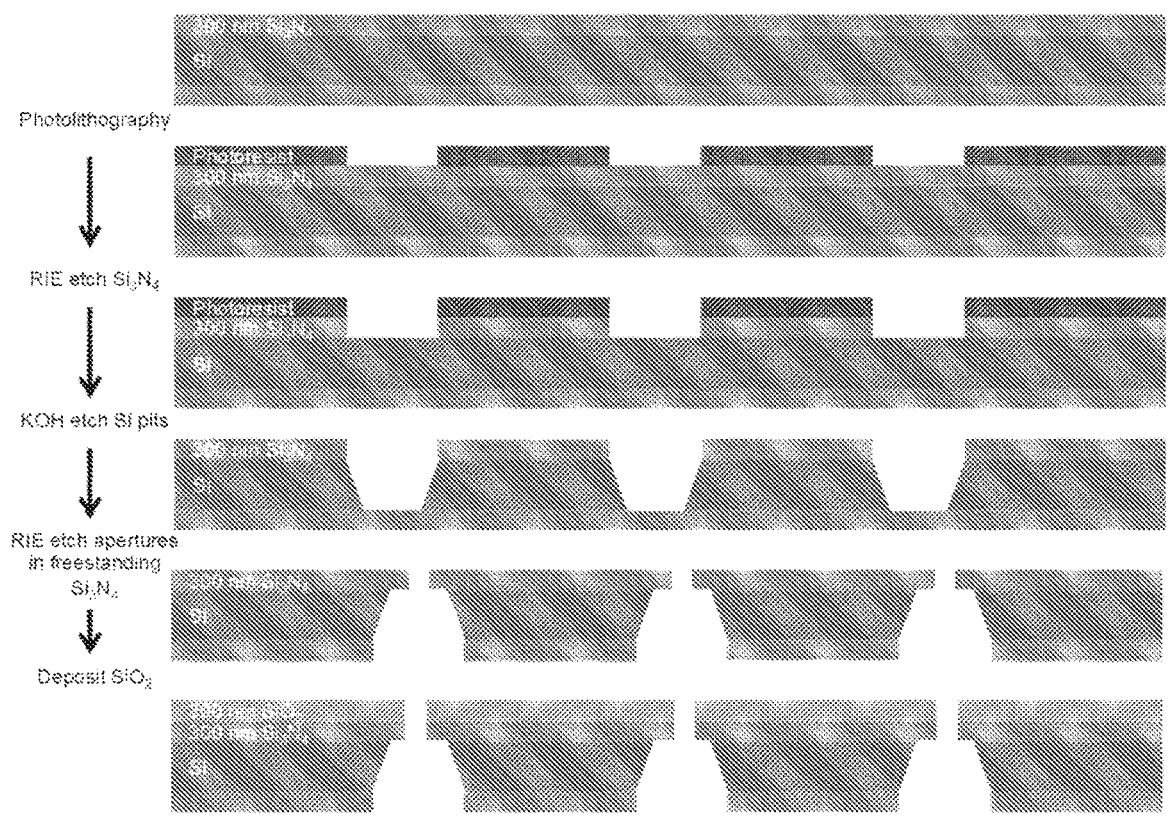
FIG. 8 shows an exemplary schematic illustration outlining fabrication steps used to create a substrate, according to some embodiments.
Figure 9:
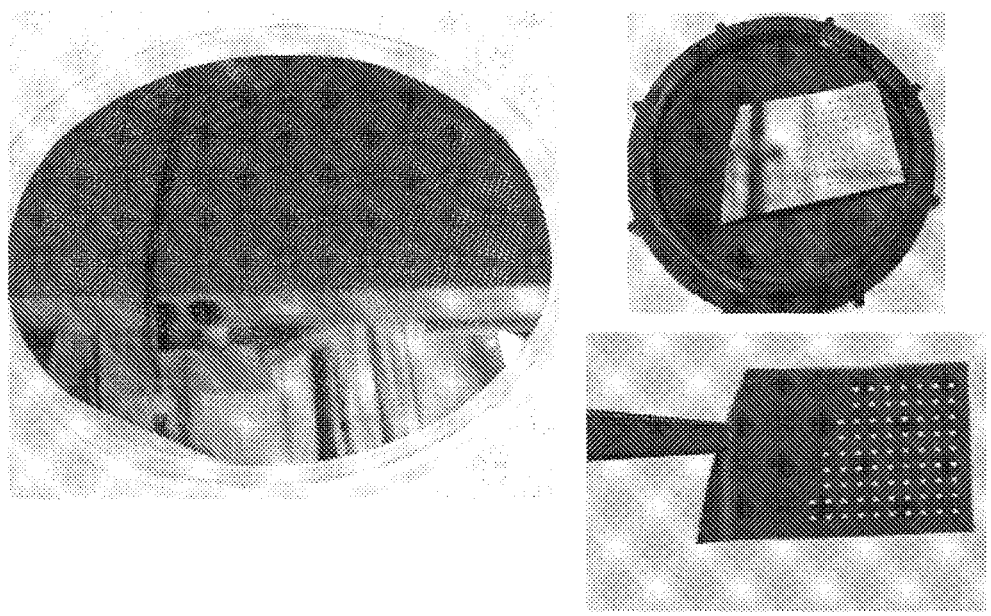
FIG. 9 shows photographs of a substrate after aperture fabrication, according to some embodiments.

FIG. 8 provides a schematic illustration outlining the fabrication steps used to create the supporting substrate. A Si wafer (<100>; 4" diameter; 500-μm thick) was first cleaned using the standard RCA cleaning protocol. A 300-nm thick layer of low stress (less than 200 MPa) $Si_3N_4$ was then grown on the top and bottom surfaces of the wafer using low-pressure chemical vapor deposition (LPCVD). Standard photolithography and reactive ion etching (RIE) were used to remove sets of 9×12 arrays of squares from the top layer of $Si_3N_4$, thus exposing the underlying Si in each square. A solution of KOH was then used to anisotropically etch the exposed Si, forming freestanding $Si_3N_4$ membranes (about 250×250 $\mu m^2$). A second round of photolithography and RIE was done on the freestanding $Si_3N_4$ membranes to form circular apertures (5, 10, 20, 30, or 50 μm in diameter) at the center of each membrane. After aperture formation, the wafer was thoroughly cleaned using a piranha etch solution. FIG. 9 shows photographs of the substrate wafer after aperture fabrication. Finally, a 300-nm thick layer of $SiO_2$ was deposited on top of the aperture-containing $Si_3N_4$ membranes using plasma-enhanced chemical vapor deposition (PECVD). The following PECVD recipe was used to form the $SiO_2$ layer: 10 sccm $SiH_4$; 1420 sccm $N_2O$; 392 sccm $N_2$; pressure=900 mTorr; power=30 W; platen temperature=300° C.; lid temperature=250° C.; deposition rate=56 nm/min.; and refractive index=1.485. All the steps outlined above were completed inside a clean room.

2. Graphene Synthesis

Continuous sheets of polycrystalline graphene (Gr), consisting of single grains between about 200-3500 μm in diameter, were synthesized on Cu foils using low-pressure chemical vapor deposition. A strip of 25-μm thick Cu foil (Alfa Aesar, 99.8%), 2×7 $cm^2$ in area, was first washed in 1.0 N HCl, then sonicated in acetone for 15 min., triple rinsed with isopropyl alcohol, and blown dry with $N_2$. The strip was then inserted into a quartz tube (22-mm inner diameter), and the pressure in the tube was lowered to less than 50 mTorr using a scroll pump. Ar (300 sccm) was flowed through the tube for 5 min., after which the pressure of the tube was then increased to about 750 mTorr using a metering valve located between the end of the tube and the pump. While maintaining an Ar flow rate of 300 sccm, a Lindberg/Blue M Mini-Mite horizontal tube furnace was used to increase the temperature of the system to 1,070° C. over a period of 35 min. The Cu foil was annealed at 1,070° C. for 5 min. Gr synthesis was begun with the introduction of $H_2$ and diluted $CH_4$ (500 ppm in a balance of Ar), each at a flow rate of 20 sccm. The synthesis reaction was run for 200 min. to ensure complete Gr coverage on the bottom side of the copper foil, i.e. the side of the foil facing the bottom of the quartz tube. The reaction was arrested by cooling the system for 45 min. using an external fan until the temperature of the furnace was less than 30° C. All gases used in the synthesis of Gr were ultra high purity grade.

3. Graphene Transfer Methods a. Wet Transfer Method

Figure 10:
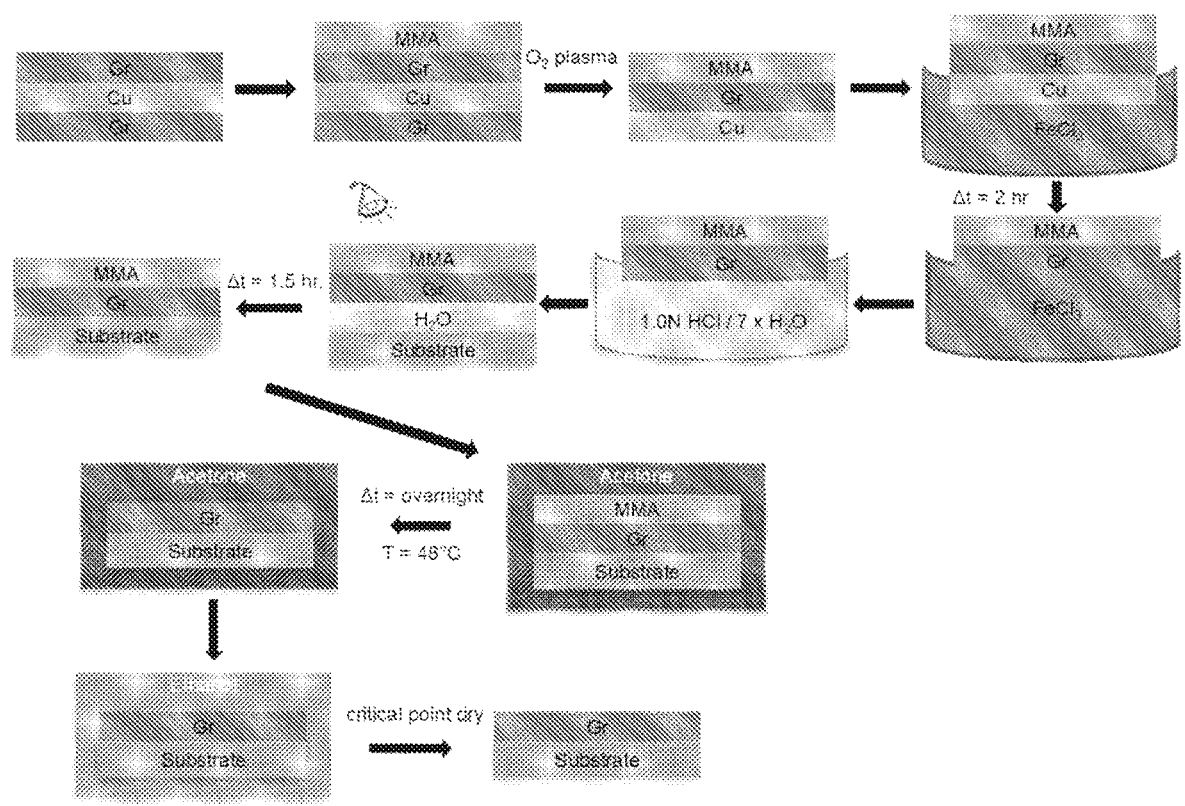
FIG. 10 shows a schematic illustration outlining steps of a graphene wet transfer method, according to some embodiments.

FIG. 10 shows a schematic illustration outlining the steps of the graphene wet transfer method. A section of graphene-containing copper foil (Gr/Cu) was first placed on a piece of wax paper. The wax paper was cut so that it was about 5-10 mm longer around its perimeter than the piece of Gr/Cu. The Gr/Cu and wax paper were then placed on a 2"×3", 1 mm thick glass microscope slide. Using scotch tape, the edges of the Gr/Cu and wax paper were taped firmly to the glass slide. Methyl methacrylate (MMA) polymer solutions (2%, 4%, and 6% MMA in ethyl lactate diluted from a stock solution of MicroChem 9% MMA 8.5 in ethyl lactate) were each spun on the Gr/Cu for 30 seconds at 3000 RPM. Then the sample was baked at 180° C. on a hot plate for 3 minutes to cure the MMA layers. To free the MMA-coated Gr/Cu, a scalpel was used to cut along the perimeter of the wax paper just outside of Gr/Cu region. Using scissors, the Gr/Cu was cut just inside of the non-taped boundary, which allowed for the removal of both the scotch tape and the wax paper. To remove Gr on the side of the Cu foil not covered by MMA, the MMA/Gr/Cu stack was taped on a glass slide such that the MMA side was facing down. The same steps described above were used to tape the stack to the glass slide. The unwanted Gr was removed by $O_2$ plasma (100 W, 1-2 minutes). Scissors were then used to cut a piece of the MMA/Gr/Cu stack to fit the size specifications of the target substrate. After the stack was properly sized, the remaining tape was cut off and the stack was freed from the wax paper. The stack was then picked up at one of its corners using tweezers and gently placed in a bath of ferric chloride solution ($FeCl_3$, Transene CE-100) with the bare Cu side facing down on the solution's surface. The stack was left in $FeCl_3$ for 2 hr. to ensure that all the Cu was removed. Once the Cu was completely etched, the MMA/Gr stack was then moved to a deionized water bath (Millipore, 18 MOhms) using a piece of bare Si wafer that had been cleaned using $O_2$ plasma to make its surface hydrophilic. After several minutes in the water bath, the same piece of Si wafer was used to move the stack to a solution of 1.0 N HCl and then to 6 more deionized water baths. While the stack was in the last of the deionized water baths, it was scooped out using the target substrate ($SiO_2/Si_3N_4$ chip with an array of 108 apertures), which had previously been $O_2$ plasma cleaned for 1 minute at 30 W. The MMA/Gr/substrate stack was then placed under a halogen lamp for a minimum of 90 minutes to allow the water to migrate out from underneath the stack and to eventually evaporate.

Figure 11:
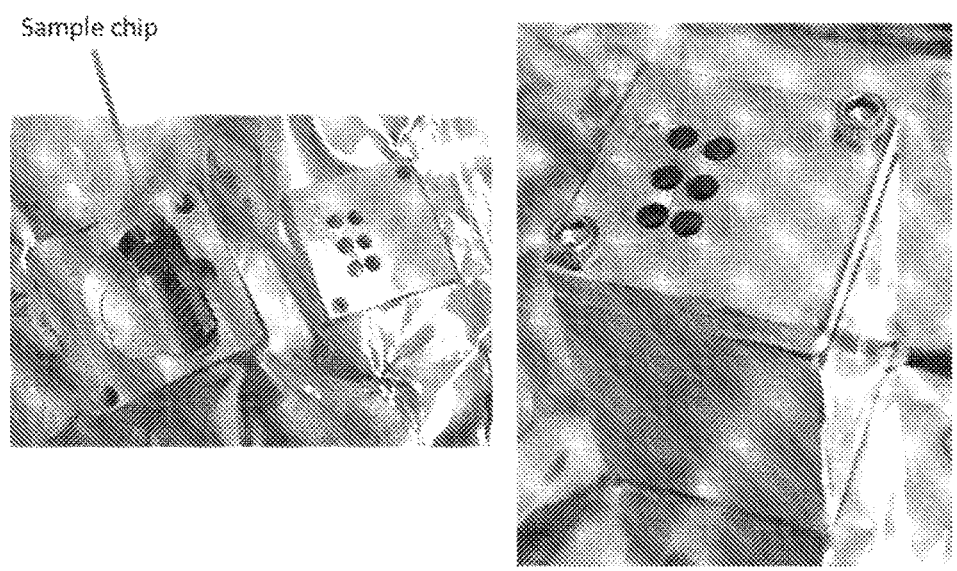
FIG. 11 shows photographs of a solvent-exchange jar used as part of a graphene wet transfer method, according to some embodiments.

Once dry, the MMA layer was dissolved using acetone. A homemade aluminum jar (see FIG. 11) was used to house the substrate during this process. The substrate was first placed in the jar, and the jar was then placed inside a large beaker. Acetone was added slowly and gently to the beaker until the jar was fully submerged. The beaker was placed on a hotplate set to 48° C. and left there overnight. Acetone was then exchanged with 200-proof ethanol to facilitate critical point drying. The exchange was accomplished by removing the jar from the acetone-containing beaker and transferring it to a beaker containing ethanol. The jar was allowed to sit in ethanol for 5 minutes in order for the acetone in the jar to be completely replaced with ethanol. This process was repeated 3 more times with ethanol to ensure the substrate inside the jar was immersed solely in ethanol. A critical point dryer (Tousimis 931 Series) was then used to remove the ethanol. Ethanol was replaced with liquid $CO_2$ over the course of three, 30 min. cycles. Three cycles provided extra assurance that all the ethanol was replaced with liquid $CO_2$ during the drying process.

b. Dry Transfer Method

An about 1.5×2 $cm^2$ piece of graphene on Cu foil (Gr/Cu) was first spin coated with 4% (w/w) polymethyl methacrylate (PMMA) in anisole (MicroChem 950PMMA A) for 40 sec. at 1,000 RPM. The PMMA was cured at room temperature for 60 min. Graphene on the backside of the foil was removed by $O_2$ plasma (100 W, 1 min.). The PMMA/Gr/Cu foil stack was then pressed onto the bottom of a PDMS support frame containing an about 1×1.5 $cm^2$ rectangular hole. The Cu foil was etched in ferric chloride ($FeCl_3$, Transene CE-100) for 30 min., then rinsed in deionized $H_2O$ (Millipore, 18 MOhm) for 15 min., 2.0 N HCl for 30 min., and finally deionized $H_2O$ again for 15 min. A glass microscope slide was used to transfer the PDMS/PMMA/Gr stack between solutions because of the ease at which the PMMA/Gr stack ripped while being pulled off of air/liquid interfaces. After the final deionized $H_2O$ rinse, the stack was lifted out of the solution with a glass microscope slide. Several milliliters of ethanol (200 proof) were then pipetted around the PDMS frame to replace the water trapped underneath the stack with ethanol. This was done to lower the surface tension and help prevent the stack from tearing. The stack was then carefully pulled off the microscope slide so as to avoid tearing the PMMA/Gr and gently blown dry with $N_2$ for about 5 min. A $SiO_2/Si_3N_4$ substrate with a 9×12 array of circular apertures (diameter=10 or 30 μm) was placed face down on the PDMS/PMMA/Gr stack such that the graphene was in contact with the side of the substrate opposite to that with the pits. The PDMS frame was cut from the PMMA/Gr using a finely pointed scalpel. To promote graphene adhesion the sample was placed in a home-built acetone humidor for 15 min. followed by heating the sample to 180° C. for 2 hr. in an atmosphere of Ar (500 sccm) at a pressure of about 500 Torr. The PMMA was thermally removed by heating the sample to 350° C. for 4 hr. in an atmosphere of $H_2$ (500 sccm) and Ar (500 sccm) at a pressure of about 1 Torr.

4. Additional Images and Data a. Cu Etchant Used for Graphene Transfer

Figure 12:
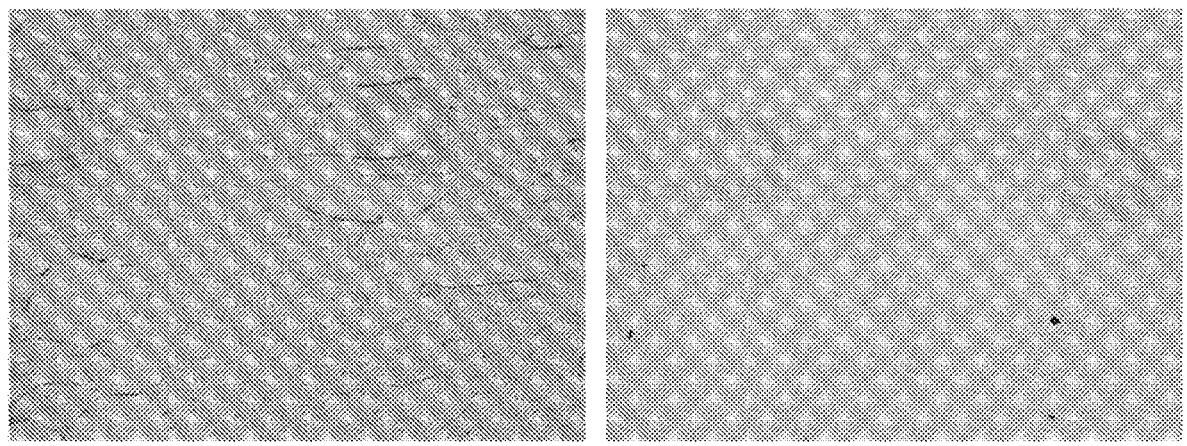
FIG. 12 shows optical micrographs of graphene that was transferred using ammonium persulfate (left) and ferric chloride (right), according to some embodiments.

It was found that using ferric chloride as the Cu etchant allowed graphene to be transferred to the substrates with fewer tears and rips than if ammonium persulfate (purchased as a salt and dissolved in deionized $H_2O$ to form a 0.1M solution) was used. FIG. 12 shows optical micrographs that qualitatively compare graphene that had been transferred to the substrates using ammonium persulfate (left) and ferric chloride (right). The ferric chloride transfer gave better and more consistent adhesion between graphene and the substrate surface, with only one large tear in the upper right corner of the image versus the many tears and dark scrolls seen in the ammonium persulfate transfer image.

b. Broken Graphene Membranes

Figure 13:
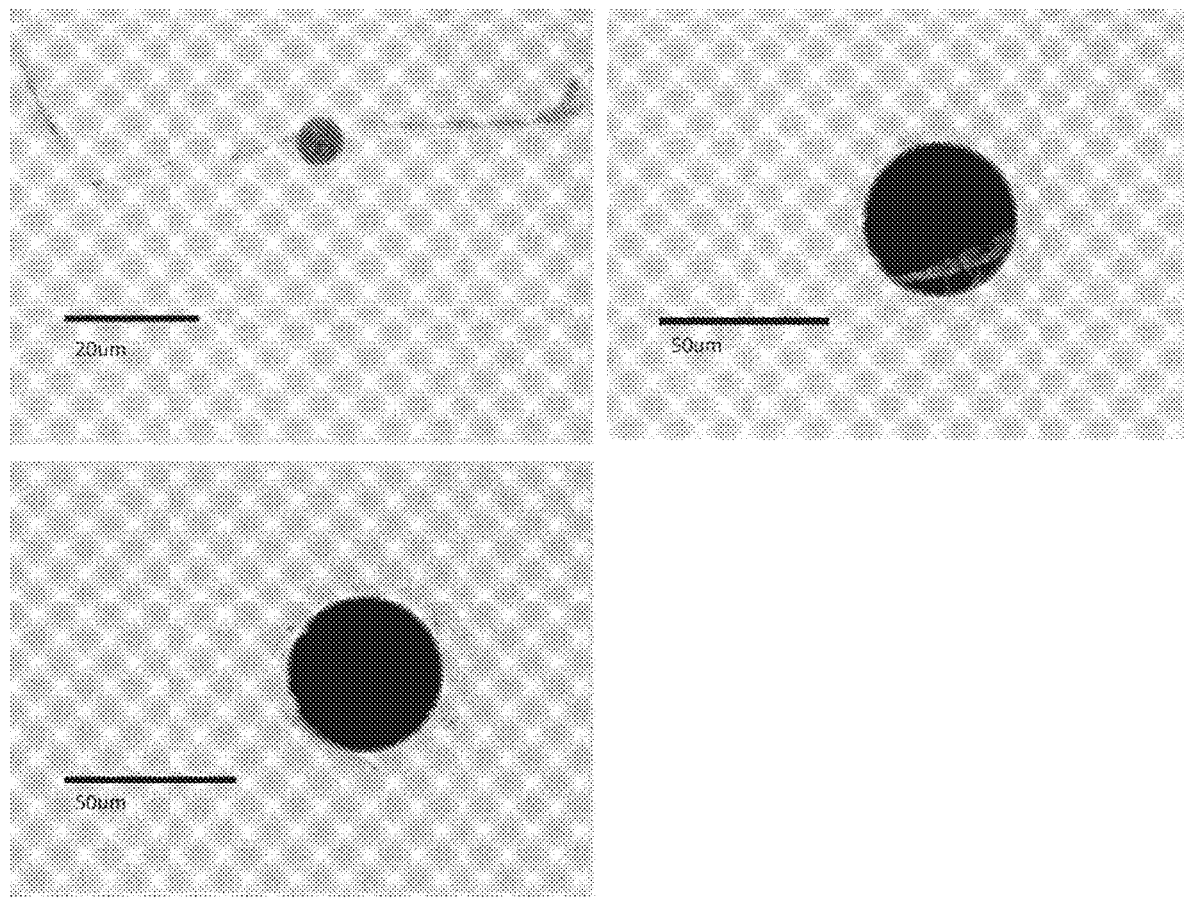
FIG. 13 shows optical micrographs of broken graphene membranes, according to some embodiments.

In FIG. 13, optical micrographs show broken graphene membranes that were typically encountered while attempting to suspend graphene over large apertures.

c. Raman Data from a 30-μm Suspended Bilayer Graphene Device

Figure 14:
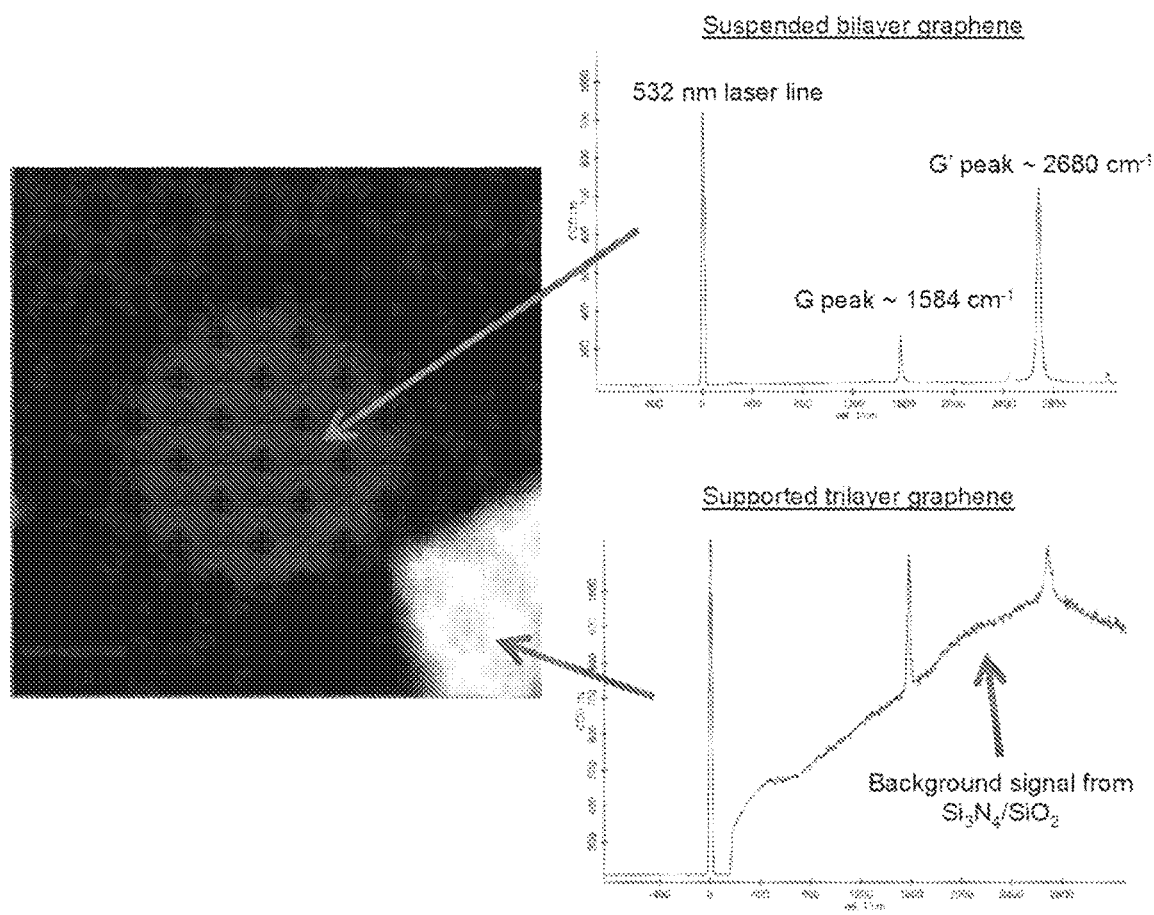
FIG. 14 shows Raman map and point spectra of a 30-micron suspended bilayer graphene device, according to some embodiments.

FIG. 14 shows Raman map and point spectra of a 30-μm suspended bilayer graphene device. The top point spectrum was taken in the middle of the suspended bilayer area, whereas the bottom point spectrum was taken in an area containing supported trilayer graphene. The laser excitation photon energy was 2.33 eV at 8 mW, and the laser spot size was 1-2 μm. The successfully suspended bilayer graphene membrane exhibited rotational disorder.

d. Laser-Induced Rupturing of Suspended Graphene Membranes

Figure 15:
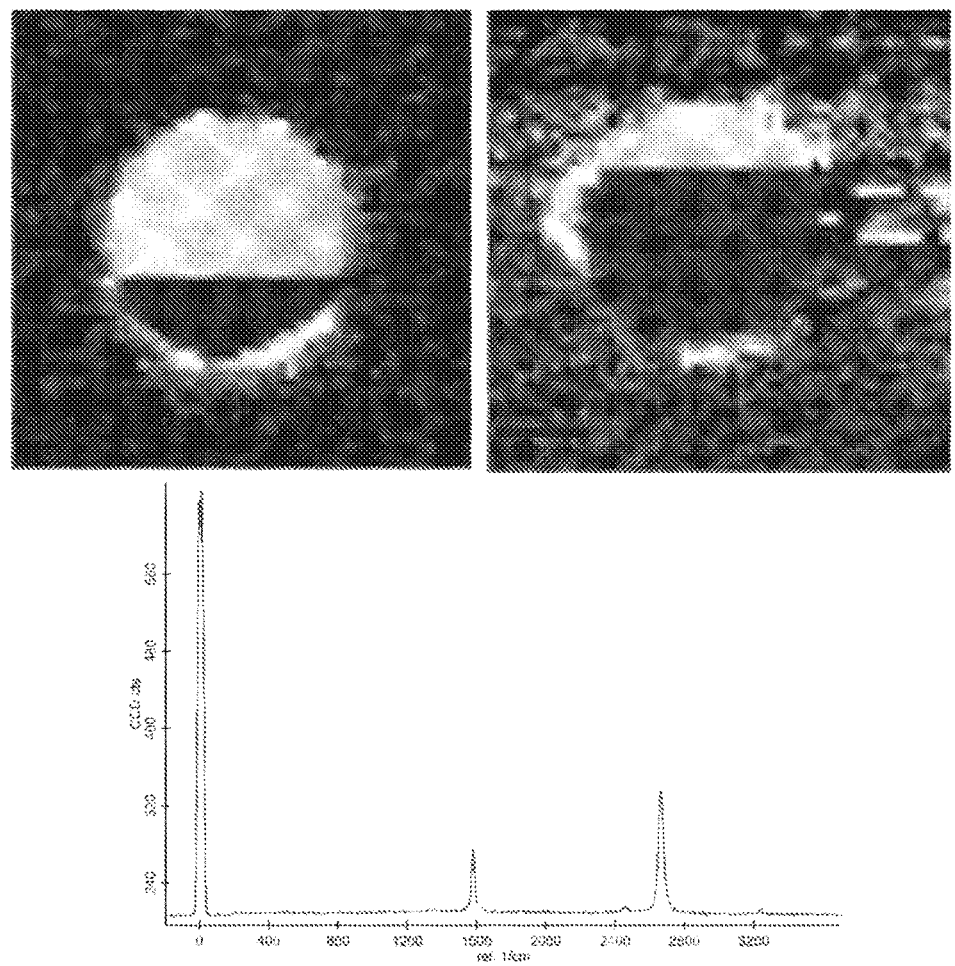
FIG. 15 shows Raman maps and point spectra of two broken 30-micron suspended monolayer graphene devices, according to some embodiments.

While conducting Raman analysis, if the laser intensity was too high, the suspended graphene membranes were easily ruptured (possibly due to localized heating). This was especially common during Raman area scans on 30-μm diameter freestanding graphene membranes. FIG. 15 shows Raman maps and a point spectrum of two broken 30-μm suspended monolayer graphene devices. Each suspended graphene membrane broke while the data for the Raman map was being collected. Laser excitation photon energy=2.33 eV at 8 mW and laser spot size=1-2 μm. A Raman point spectrum of the left freestanding graphene membrane indicated that it was monolayer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system, comprising:
   a layer comprising graphene, wherein the layer comprising graphene has a first surface and a second, opposed surface;
   a light-absorbing complex coupled to the first surface of the layer comprising graphene;
   an electron donor; and
   a first substrate layer comprising at least one aperture, wherein the layer comprising graphene fully covers the at least one aperture, and wherein at least a portion of the first substrate layer is directly adjacent the layer comprising graphene.

2. The system of claim 1, further comprising a catalytic complex coupled to the second surface of the layer comprising graphene.

3. The system of claim 2, wherein the catalytic complex is capable of catalyzing the formation of $H_2$, NADH, and/or NADPH.

4. The system of claim 1, wherein the light-absorbing complex comprises chlorophyll, zinc phthalocyanine, zinc porphyrin, zinc heme, zinc TPP, beta-carotene, P680, and/or plastoquinone A.

5. The system of claim 1, wherein the electron donor is coupled to the light-absorbing complex.

6. The system of claim 1, further comprising an electron acceptor.

7. The system of claim 1, wherein the light-absorbing complex and/or electron donor are part of a protein complex.

8. The system of claim 7, wherein the protein complex is photosystem II (PSII).

9. The system of claim 1, wherein the first substrate layer comprises a metal and/or a semiconductor.

10. The system of claim 1, wherein the graphene is monolayer graphene.

11. The system of claim 1, wherein the layer comprising graphene comprises a plurality of holes, and wherein the holes have an average diameter of about 5 microns or less.

12. The system of claim 1, wherein the at least one aperture has a diameter of at least about 100 nm.

13. The system of claim 1, further comprising a second substrate layer positioned adjacent the first substrate layer.

14. The system of claim 13, further comprising a third substrate layer positioned adjacent the second substrate layer.

15. The system of claim 1, further comprising a battery and/or potentiostat in electrical communication with the layer comprising graphene and with a reference electrode.

16. The system of claim 1, further comprising a battery in electrical communication with the layer comprising graphene and the first substrate layer or with the layer comprising graphene and an electrode.

17. The system of claim 1, further comprising a catalytic complex coupled to the first surface of the layer comprising graphene.

18. The system of claim 16, wherein the system is a field-effect transistor.

19. The system of claim 2, wherein the catalytic complex comprises a hydrogenase, platinum, and/or at least one nanoparticle.

20. The system of claim 1, wherein the electron donor comprises an oxygen-evolving complex.

* * * * *